United States Patent
Rankovic et al.

(10) Patent No.: US 7,326,715 B2
(45) Date of Patent: Feb. 5, 2008

(54) 4-PHENYL-6-SUBSTITUTED-PYRIMIDINE-2-CARBONITRILE DERIVATIVES

(75) Inventors: Zoran Rankovic, Newhouse (GB); Jiaqiang Cai, Newhouse (GB)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 11/524,841

(22) Filed: Sep. 21, 2006

(65) Prior Publication Data
US 2007/0111992 A1 May 17, 2007

Related U.S. Application Data

(60) Provisional application No. 60/719,801, filed on Sep. 23, 2005.

(51) Int. Cl.
*C07D 239/34* (2006.01)
*C07D 239/38* (2006.01)
*C07D 239/42* (2006.01)
*A61K 31/505* (2006.01)
*A61P 9/10* (2006.01)
*A61P 19/02* (2006.01)
*A61P 19/10* (2006.01)
*A61P 29/00* (2006.01)

(52) U.S. Cl. .................. 514/269; 544/319; 544/326; 514/256

(58) Field of Classification Search .............. 544/319, 544/326; 514/269, 256
See application file for complete search history.

(56) References Cited

FOREIGN PATENT DOCUMENTS

| WO | WO 03/020278 A1 | 3/2003 |
|---|---|---|
| WO | WO 03/020287 A2 | 3/2003 |
| WO | WO 03/020287 A3 | 3/2003 |
| WO | WO 03/020721 A1 | 3/2003 |
| WO | WO 2004/000819 A1 | 12/2003 |
| WO | WO 2004/000843 A1 | 12/2003 |

OTHER PUBLICATIONS

Hou et al. Arthritis & Rheumatism, 46(3): 663-674, 2002.*
Bromme, D. et al., "Human Cathepsin O2, a Matrix Protein-degrading Cysteine Protease Expressed in Osteoclasts," *J. Biol. Chem.*, vol. 271 (1996) pp. 2126-2132.
Bromme, D. et al., "Human Cathepsin O2, a Novel Cysteine Protease Highly Expressed in Osteoclastomas and Ovary Molecular Cloning, Sequencing and Tissue Distribution," *Biol. Chem. Hoppe-Seyler*, vol. 376 (1995) pp. 379-384.
Kafienah, W. et al., "Human cathepsin K cleaves native type I and II collagens at the N-terminal end of the triple helix," *Biochem. J.*, vol. 331 (1998) pp. 727-732.
Bossard, M. J. et al., "Proteolytic Activity of Human Osteoclast Cathepsin K," *The Journal of Biological Chemistry*, vol. 271, No. 21 (1996) pp. 12517-12524.
Sukhova, G. K. et al., "Expression of the Elastolytic Cathepsins S and K in Human Atheroma and Regulation of their Production in Smooth Muscle Cells," *J. Clin. Invest.*, vol. 102, No. 3 (1998) pp. 576-583.
Xin, W-Q et al., "The Specificity and Elastinolytic Activities of Bovine Cathepsins S and H$^1$," *Archives of Biochemistry and Biophysics*, vol. 299, No. 2 (1992) pp. 334-339.
Shi, G-P et al., "Molecular Cloning and Expression of Human Alveolar Macrophage Cathepsin S, an Elastinolytic Cysteine Protease," *The Journal of Biological Chemistry*, vol. 267, No. 11 (1992) pp. 7258-7262.
Maciewicz, R. A., "A comparison of four cathepsins (B, L, N and S) with collagenolytic activity from rabbit spleen," *Biochem. J.*, vol. 267 (1988) pp. 433-440.
Sukhova, G. K., "Deficiency of cathepsin S reduces atherosclerosis in LDS receptor-deficient mice," *The Journal of Clinical Investigation*, vol. 111, No. 6 (2003) pp. 897-906.
Lindstedt, L. et al., "Cathepsins F and S block HDL$_3$-induced cholesterol efflux from macrophage foam cells," *Biochemical and Biophysical Research Communications*, vol. 312 (2003) pp. 1019-1024.
Saegusa, K. et al., "Cathepsin S inhibitor prevents autoantigen presentation and autoimmunity," *The Journal of Clinical Investigation*, vol. 110, No. 3 (2002) pp. 361-369.
Shi, G-P et al., "Cystatin C deficiency in human atherosclerosis and aortic aneurysms," *J. Clin. Invest.*, vol. 104 (1999) pp. 1191-1197.

* cited by examiner

*Primary Examiner*—Venkataraman Balasubramanian
(74) *Attorney, Agent, or Firm*—Susan Hess

(57) ABSTRACT

Disclosed herein are 4-phenyl-6-substituted-pyrimidine-2-carbonitrile derivatives having Formula I,

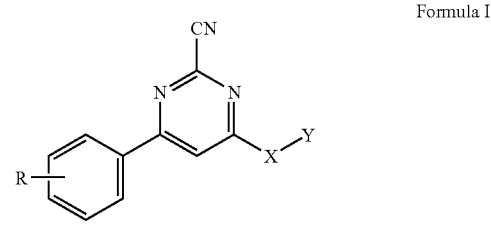

Formula I wherein each of the substituents is given the definition as set forth in the specification and claims; or a pharmaceutically acceptable salt thereof. Also disclosed are pharmaceutical compositions comprising these 4-phenyl-6-substituted-pyrimidine-2-carbonitrile derivatives and use of these 4-phenyl-6-substituted-pyrimidine-2-carbonitrile derivatives for the treatment of cathepsin K and cathepsin S related disorders, e.g. osteoporosis, atherosclerosis, inflammation and immune disorders such as rheumatoid arthritis and chronic pain.

12 Claims, No Drawings

4-PHENYL-6-SUBSTITUTED-PYRIMIDINE-2-CARBONITRILE DERIVATIVES

The invention relates to 4-phenyl-6-substituted-pyrimidine-2-carbonitrile derivatives, to pharmaceutical compositions comprising the same, as well as to the use of these derivatives for the preparation of a medicament for the treatment of cathepsin K related diseases such as osteoporosis and atherosclerosis.

Cysteine proteases represent a class of peptidases characterised by the presence of a cysteine residue in the catalytic site of the enzyme, and these proteases are associated with the normal degradation and processing of proteins. Many pathological disorders or diseases are the results of abnormal activity of cysteine proteases such as over expression or enhanced activation. The cysteine cathepsins, e.g. cathepsin B, K, L, S, V, F, are a class of lysosomal enzymes which are implicated in various disorders including inflammation, rheumatoid arthritis, osteoarthritis, osteoporosis, tumors, coronary disease, atherosclerosis, autoimmune diseases and infectious diseases.

Cathepsin K has strong collagenolytic, elastase and gelatinase activities (Bromme et al., J. Biol, Chem, 271, 2126-2132, 1996) and is predominantly expressed in osteoclasts (Bromme and Okamoto, Biol. Chem. Hopp-Seyler, 376, 379-384, 1995). It cleaves key bone matrix proteins, including collagen type I and II (Kaffienah et al., Biochem. J. 331, 727-732, 1998), gelatine, osteopontin and osteonectin, and as such is involved in extracellular matrix metabolism necessary for normal bone growth and remodelling (Bossard et al., J. Biol. Chem. 271, 12517-12524, 1996). Inhibition of cathepsin K should result in the diminution of osteoclast mediated bone resorption. Cathepsin K inhibitors may therefore represent new therapeutic agents for the treatment of disease states in man such as osteoporosis.

Sukhova et al (J. Clin. Invest. 102, 576-583, 1998) have thereafter demonstrated that cells (macrophages) that migrate into and accumulate within developing human atherosclerotic plaques also synthesize the potent elastases Cathepsin K and S. Matrix degradation, particularly in the fibrous cap of such plaques, is a crucial process in atherosclerotic lesion destabilization. Thus, the metabolism of the extracellular matrix components collagen and elastin, which confer structural integrity upon the lesion's fibrous cap, can critically influence the clinical manifestations of atherosclerosis, such as coronary artery thrombosis as a result of rupture of an atherosclerotic plaque. Inhibition of cathepsins K and/or S at sites of plaques prone to rupture may thus represent an effective way of preventing such events.

Like Cathepsin K, Cathepsin S also has potent elastolytic (Arch. Biochem. Biophys., 299, 334-339, 1992; J. Biol. Chem., 267, 7258-7262, 1992) and collagenolytic activities (Biochem. J., 256, 433-440, 1998). Diseased human arteries overexpress both cathepsin K and S and exhibit a reciprocal deficiency of cystatin C, the most abundant endogenous inhibitor of cysteine proteases (J. Clin. Invest. 102, 576-583, 1998; J. Clin. Invest. 104, 1191-1197, 1999). Sukhova et al (J. Clin. Invest. 111, 897-906, 2003) have demonstrated that deficiency of cathepsin S reduces atherosclerosis in LDL receptor-deficient mice. Bromme et al (Biochem. Biophys. Research Comm., 312, 1019-1024, 2003) also demonstrated that both Cathepsin K and S are capable of degrading HDL3 and lipid free apoA-1 in vitro. This further indicates cathepsin K and S as therapeutic target for atherosclerosis.

Cathepsin S has been shown to be a key enzyme involved in invariant chain processing in human and mouse antigen-presenting cells (J. Clin. Invest. 110, 361-369, 2002). This invariant chain processing regulates MHC class II function and is associated with autoimmune disorders. Saegusa et al (J. Clin. Invest. 110, 361-369, 2002) have thereafter demonstrated that inhibition of cathepsin S in vivo alters autoantigen presentation and development of organ-specific autoimmunity.

It has been disclosed in WO 03/020287 (Novartis Pharma GMBH) that mRNA for cathepsin S is up-regulated in animal models of chronic pain and that administration of cathepsin S inhibitors causes a reversal of mechanical hyperalgesia in these animals.

4-Amino-pyrimidine-2-carbonitrile derivatives have been disclosed as inhibitors of cathepsins K and/or S in the International Patent Application WO 03/020278 (Novartis Pharma GMBH), while structurally related 4-amino-pyrimidine-2 carbonitrile derivatives were recently disclosed in WO04/000819 (ASTRAZENECA AB) as Cathepsin S inhibitors. Pyrrolo-pyrimidines have likewise been disclosed as cathepsin K and/or S inhibitors in WO 03/020721 (Novartis Pharma GMBH) and WO 04/000843 (ASTRAZENECA AB).

It has now been found that 4-phenyl-6-substituted-pyrimidine-2-carbonitrile derivatives having the general Formula I

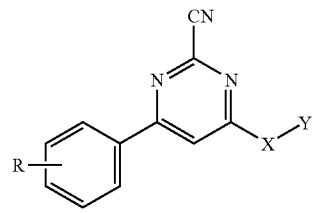

Formula I wherein

R represents 1-3 optional substituents independently selected from $(C_{1-4})$alkyl (optionally substituted with one or more halogens), $(C_{1-4})$alkyloxy (optionally substituted with one or more halogens) and halogen;

X is $NR_1$, O or S;

$R_1$ is H or $(C_{1-4})$alkyl;

Y is $(C_{1-4})$alkyl, benzyl or $(C_{2-6})$alkyl, substituted with a group selected from OH, $(C_{1-4})$alkyloxy, $NR_2R_3$, a 4-8 membered saturated heterocyclic ring comprising 1 or 2 heteroatoms selected from O, S and $NR_4$, and a 5 or 6-membered aromatic heterocyclic group comprising 1-4 N atoms; or $R_1$ and Y form together with the nitrogen to which they are bonded a 5-8 membered saturated heterocyclic ring, optionally comprising a further heteroatom selected from O, S, $NR_4$ and NO; the ring being optionally substituted with $NR_2R_3$ or with 1 to 4 $(C_{1-3})$alkyl groups;

$R_2$ and $R_3$ are independently H or $(C_{1-4})$alkyl; or $R_2$ and $R_3$ form together with the nitrogen to which they are bonded a 4-8 membered saturated heterocyclic ring, optionally comprising a further heteroatom selected from O, S and $NR_4$;

$R_4$ is H, $(C_{1-6})$alkyl, $(C_{3-6})$cycloalkyl, $(C_{3-6})$cycloalkyl$(C_{1-4})$alkyl, $(C_{1-4})$alkyloxy$(C_{1-4})$alkyl, benzyl, amido$(C_{1-4})$alkyl, $(C_{1-6})$alkyloxycarbonyl$(C_{1-4})$alkyl or carboxy$(C_{1-4})$alkyl;

or a pharmaceutically acceptable salt thereof, are inhibitors of cathepsin K and cathepsin S and can therefore be used for the preparation of a medicament for the treatment of cathepsin K and cathepsin S related disorders, e.g. atherosclerosis, bone diseases such as osteoporosis, inflammation and immune disorders such as rheumatoid arthritis and multiple sclerosis, and chronic pain such as neuropathic pain.

The term $(C_{1-6})$alkyl, as used in the definition of formula I, means a branched or unbranched alkyl group having 1-6 carbon atoms, like hexyl, pentyl, 3-methyl-butyl, butyl, isobutyl, tertiary butyl, propyl, isopropyl, ethyl and methyl.

The term $(C_{1-4})$alkyl means a branched or unbranched alkyl group having 1-4 carbon atoms, like butyl, isobutyl, tertiary butyl, propyl, isopropyl, ethyl and methyl.

The term $(C_{2-6})$alkyl, as used in the definition of Y of formula I, likewise means a branched or unbranched alkyl group having 2-6 carbon atoms, like hexyl, pentyl, 3-methyl-butyl, butyl, isobutyl, tertiary butyl, propyl, isopropyl and ethyl.

The term $(C_{3-6})$cycloalkyl means a cycloalkyl group having 3-6 carbon atoms, such as cyclohexyl, cyclopentyl, cyclobutyl and cyclopropyl.

In the definition of formula I $R_2$ and $R_3$ can form together with the nitrogen to which they are bonded a 4-8 membered saturated heterocyclic ring, such as an azetidine, a pyrrolidine, a piperidine, or a 1H-azepine ring. Such rings may contain 1 or more additional heteroatoms selected from O, S or $NR_5$ to form rings such as a morpholine, a thiomorpholine, a hexahydro-1,4-oxazepine, a piperazine, a homopiperazine, an imidazolidine or a tetrahydrothiazole ring. The term 4-8 membered saturated heterocyclic ring comprising 1 or 2 heteroatoms selected from O, S and $NR_4$, as used I the definition of Y, is exemplified by rings such as morpholin-4-yl, piperazin-4-yl, pyrrolidin-1-yl and piperidin-1yl.

The term 5- or 6-membered aromatic heterocyclic group containing 1-4 N atoms, as used in the definition of Y of formula I, is exemplified by rings such as pyridyl, pyrrolyl, imidazolyl, pyrazinyl and tetrazol-5-yl.

In the definition of formula I $R_1$ and Y can form together with the nitrogen to which they are bonded a 5-8 membered heterocyclic ring, optionally comprising a further heteroatom selected from O, S, $NR_4$ and NO. Examples of such rings are piperidin-1-yl, piperazin-1-yl, 4-oxo-piperazin-1-yl and diazepan-1-yl.

The term halogen means F, Cl, Br, or I. When halogen is a substituent at an alkyl group, F is preferred. A preferred halogen substituted alkyl group is trifluoromethyl.

Preferred in the invention are those 4-phenyl-6-substituted-pyrimidine-2-carbonitrile derivatives according to formula I wherein R represents a trifluoromethyl substituent at the meta position of the 4-phenyl group.

Further preferred are the compounds wherein X is $NR_1$.

Especially preferred 4-phenyl-6-substituted pyrimidine-2-carbonitrile derivatives of the invention are:

4-(piperazin-1-yl)-6-(3-trifluoromethylphenyl)-pyrimidine-2-carbonitrile;
4-(4-cyclopropyl-piperazin-1-yl)-6-(trifluoromethylphenyl)-pyrimidine-2-carbonitrile;
4-[1,4]diazepan-1-yl-6-(3-trifluoromethylphenyl)-pyrimidine-2-carbonitrile;
4-[methyl-(1-methyl-piperidin-4-yl)-amino]-6-(3-trifluoromethylphenyl)-pyrimidine-2-carbonitrile;
4-[(1H-tetrazol-5-ylmethyl)-amino]-6-(3-trifluoromethylphenyl)-pyrimidine-2-carbonitrile;
4-(4-methoxy-3-trifluoromethylphenyl)-6-piperazin-1-yl-pyrimidine-2-carbonitrile;
4-(2-piperidin-1-yl-ethoxy)-6-(3-trifluoromethylphenyl)-pyrimidine-2-carbonitrile;
4-[4-(2-methoxy-ethyl)-piperazin-1-yl]-6-(3-trifluoromethylphenyl)-pyrimidine-2-carbonitrile;
4-(4-carbamoylmethyl-piperazin-1-yl)-6-(3-trifluoromethylphenyl)-pyrimidine-2-carbonitrile;
4-(4-isopropyl-piperazin-1-yl)-6-(trifluoromethylphenyl)-pyrimidine-2-carbonitrile;
4-[4-(2-carboxyethyl)-piperazin-1-yl]-6-(3-trifluoromethylphenyl)-pyrimidine-2-carbonitrile;
4-(4-cyclopropylmethyl-piperazin-1-yl)-6-(trifluoromethylphenyl)-pyrimidine-2-carbonitrile;
4-(3,3,4-trimethyl-piperazin-1-yl)-6-(3-trifluoromethylphenyl)-pyrimidine-2-carbonitrile;
4-(4-methyl-[1,4]diazepan-1-yl)-6-(3-trifluoromethylphenyl)-pyrimidine-2-carbonitrile;
4-(carboxymethyl-amino)-6-(3-trifluoromethylphenyl)-pyrimidine-2-carbonitrile;
4-(2-morpholin-4-yl-ethoxy)-6-(3-trifluoromethylphenyl)-pyrimidine-2-carbonitrile;
4-(2-diethylamino-ethoxy)-6-(3-trifluoromethylphenyl)-pyrimidine-2-carbonitrile.

The invention provides in a further aspect pharmaceutical compositions comprising a 4-phenyl-6-substituted-pyrimidine-2-carbonitrile derivative having general formula I, or a pharmaceutically acceptable salt thereof, in admixture with pharmaceutically acceptable auxiliaries.

The 4-phenyl-6-substituted-pyrimidine-2-carbonitrile derivatives of general Formula I can be prepared by the use of methods known in the art of organic chemistry in general. For example, compounds of general formula I wherein X represents $NR_1$, and $R_1$, R and Y have the meaning as previously defined, may be prepared as depicted in Scheme 1. Reaction of 2-methylsulfanyl-4,6-dichloropyrimidine (II) with an amine of formula $R_1$—NH—Y, wherein any further functional groups present in Y may carry an appropriate protecting group, provides compounds with general formula (III). Oxidation of a sulfide of formula (III) with an oxidation reagent, e.g. OXONE®, metachloroperoxybenzoic acid (MCPBA), hydrogen peroxide, $NaIO_4$, in a suitable solvent, e.g. dichloromethane, methanol, acetonitrile or water or in a mixture these solvents, yields a sulphone of formula (IV). Palladium or other transition metal catalysed cross coupling of a sulphone of formula (IV) with an aryl boronic acid or other aryl metallic reagent affords a biaryl derivative of formula (V), which, upon substitution of the sulfonyl moiety of (V) with cyanide, e.g. sodium cyanide, and subsequent removal of any protecting group, provides a 4-phenyl-6-substituted-pyrimidine-2-carbonitrile derivative of general formula (VI).

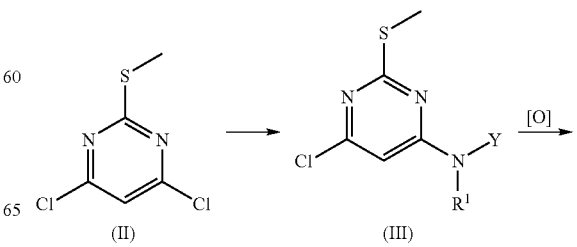

Scheme 1

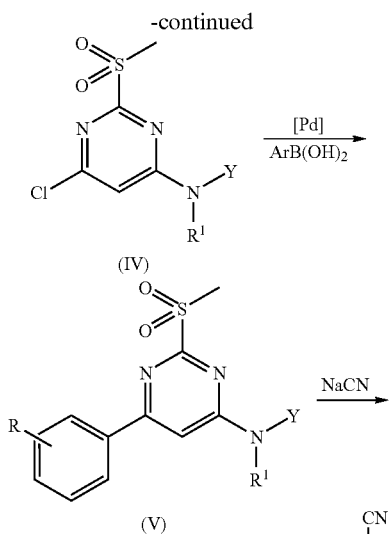

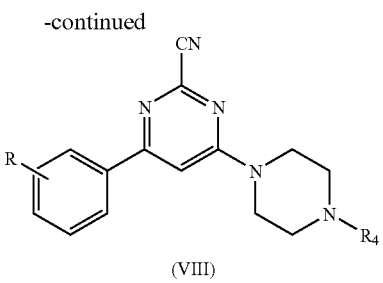

Alternatively, compound of formula (VIII) can be prepared from compounds of formula (VII) by reductive amination using an aldehyde and a reducing agent such as sodium cyanoborohydride, sodium triacetoxyborohydride or a resin bond reducing agent (Scheme 3).

Scheme 3

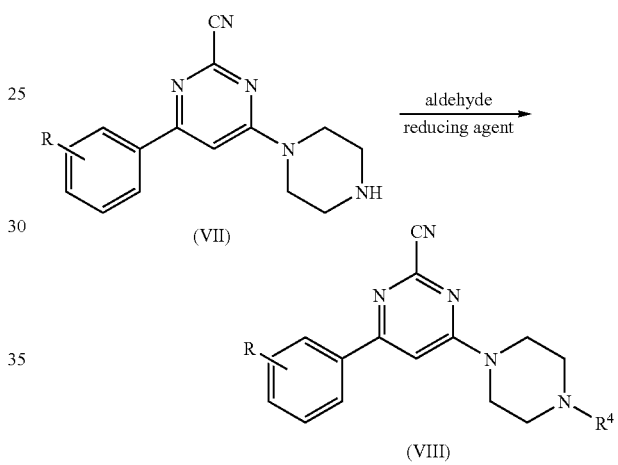

Compounds of formula (VI) may also represent intermediate compounds from which further compounds of the invention can be prepared. An example thereof is depicted in Scheme 2, wherein compounds of formula (VI) wherein $R_1$ and Y form together with the nitrogen to which they are bonded a piperazine ring, protected by a tert-butyloxycarbonyl (Boc) group, are deprotected to compounds of formula (VII), which upon N-alkylation with an alkyl halide of formula $R_4$—X, wherein $R_4$ has the previously defined meaning and X is halogen, in the presence of a base, e.g. DIPEA, $K_2CO_3$ in a suitable solvent, e.g. acetonitrile or dimethylformamide provides compounds with general formula (VIII).

In another method, as depicted in Scheme 4, substitution of 2-methylsulfanyl-4,6-dichloropyrimidine with an hydroxyethylamine provides compounds of formula (IX), which can be converted using a Suzuki coupling reaction with a boronic acid to biaryl derivatives of formula (X). Oxidation of the sulfide group in (X) produces sulfones of formula (XI) as product. Subsequent cyanation of the sulphone as described in Scheme 1 produces a nitrile of formula (XII). Oxidation of the primary alcohol in compounds of formula (XII) by the use of Dess-Martin or other reagents, provides an aldehyde of formula (XIII). Reductive amination of (XIII) with a primary or secondary amine of formula $HNR_2R_3$ and the use of sodium triacetoxyborohydride or another reducing reagent provides compounds of formula (XIV) as further compounds of the invention.

Scheme 2

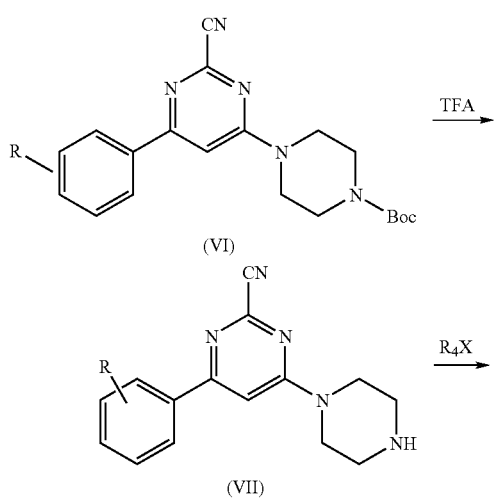

Scheme 4

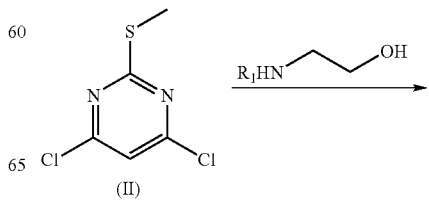

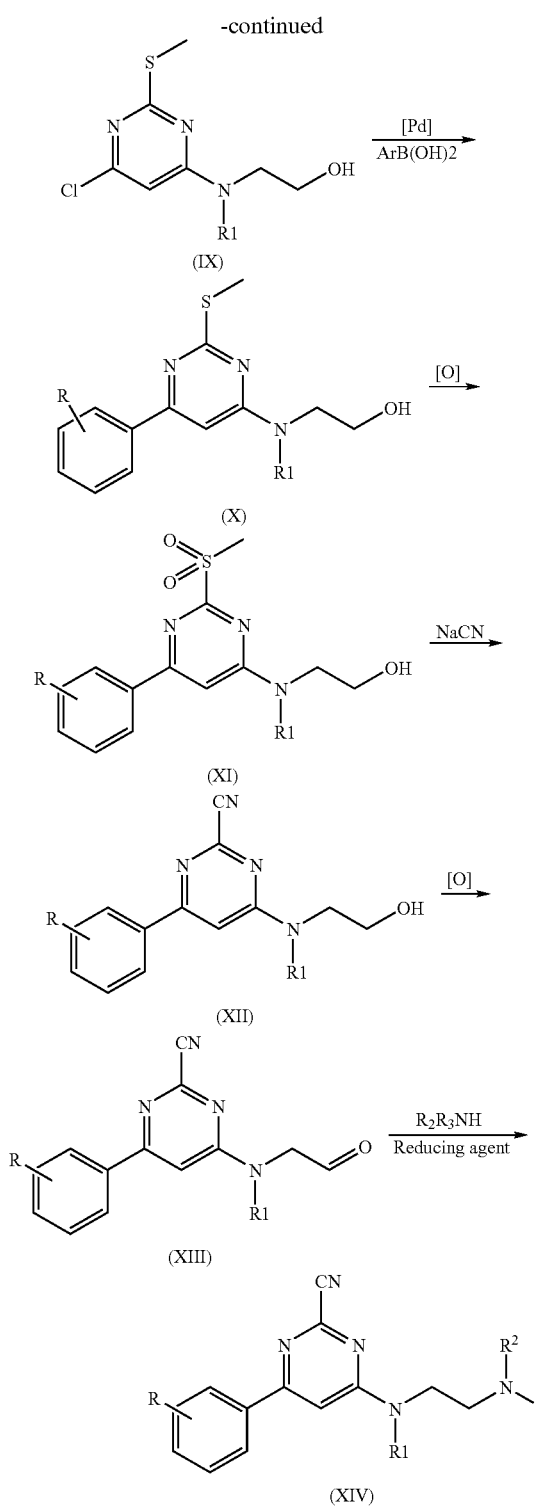

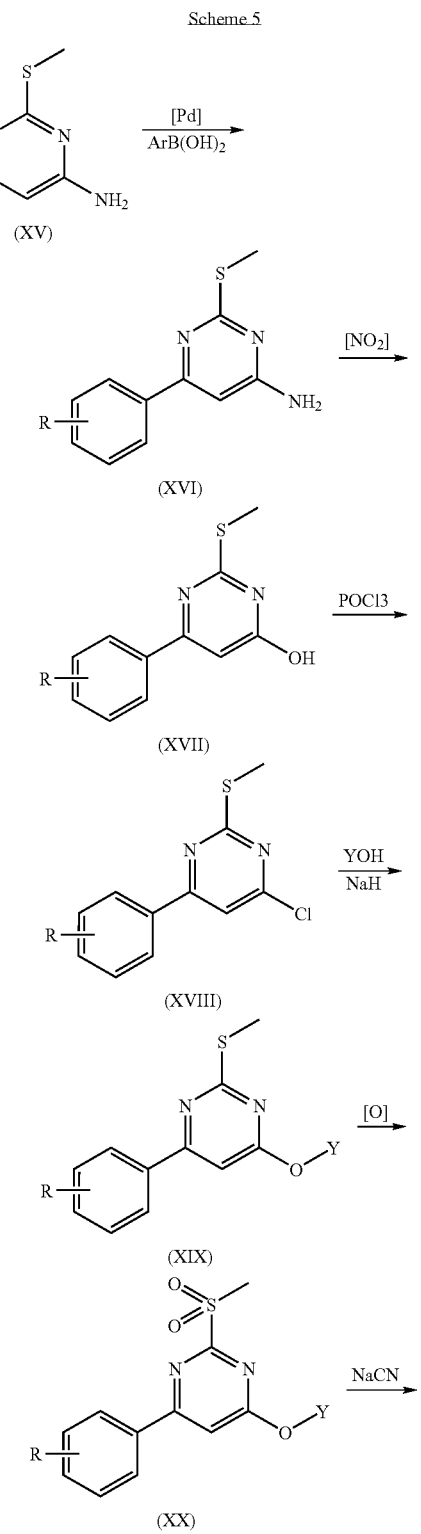

sequent coupling reaction of (XVIII) with an alcohol using sodium hydride as a base yields compounds of formula (XIX) as the product. Oxidation of the sulfide to the sulphone (XX) and subsequent cyanation of the sulphone leads to further 2-cyanopyrimidine derivatives (XXI) according to the invention.

In yet another method as depicted in Scheme 5, starting from 4-amino-2-methylsulfanyl-6-chloropyrimidine (XV), Suzuki or another type of transition metal catalysed cross coupling reaction generates a biaryl derivative of formula (XVI), the 6-amino group of which can be converted to a hydroxyl through diazotisation to produce a compound of formula (XVII), which upon treatment with POCl$_3$ gives a 4-chloro-pyrimidine derivative of formula (XVIII). The sub-

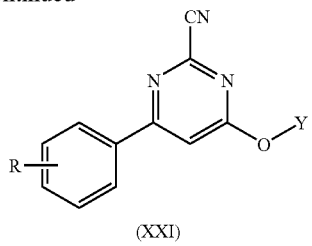

(XXI)

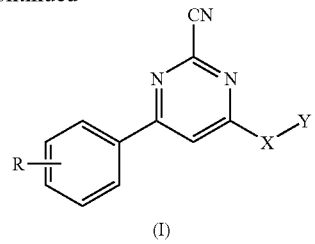

(I)

In another method, compounds of general formula (I) can be synthesised according to Scheme 6. Treatment of a compound of formula (XXI) with hydrochloric acid in methanol at refluxing temperature converts the nitrile moiety to a methyl ester with concomitant removal of benzyl group to give compounds of formula (XXII). Aminolysis and subsequent treatment with POCl$_3$ produces the 6-chloride derivatives of formula (XXIV) as key intermediates, from which compounds of the invention of general formula I are obtained by reaction with nucleophiles of general formula H—X—Y, wherein X and Y have the meanings as previously defined.

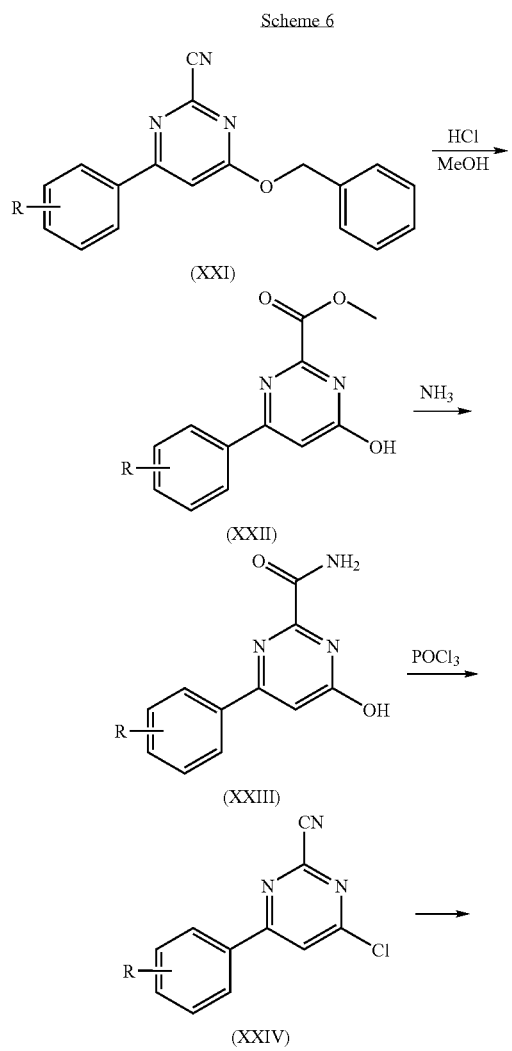

In the preparation of a 4-phenyl-6-substituted-pyrimidine-2-carbonitrile derivatives of general Formula I in which the Y contains a basic amine nitrogen atom (either in the form of NR$_2$R$_3$ or NR$_4$), such a nitrogen is to be temporarily protected, such as for example by the acid labile t-butyloxycarbonyl (Boc) group protecting group. Other suitable protecting groups for functional groups which are to be temporarily protected during syntheses, are known in the art, for example from Wuts, P. G. M. and Greene, T. W.: *Protective Groups in Organic Synthesis*, Third Edition, Wiley, New York, 1999.

The compounds of the invention, which can be in the form of a free base, may be isolated from the reaction mixture in the form of a pharmaceutically acceptable salt. The pharmaceutically acceptable salts may also be obtained by treating the free base of formula I with an organic or inorganic acid such as, but not limited to, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulphonic acid, fumaric acid, succinic acid, tartaric acid, citric acid, benzoic acid, and ascorbic acid.

Compounds of the invention may exist in solvated as well as in unsolvated forms, including hydrated forms. In general, the solvated forms are equivalent to unsolvated forms and are intended to be encompassed within the scope of the present invention.

Compounds of the present invention may exist as amorphous forms, but also multiple crystalline forms may be possible. In general, all physical forms are equivalent for the uses contemplated by the present invention and are intended to be within the scope of this invention.

The 4-phenyl-6-substituted-pyrimidine-2-carbonitrile derivatives of the invention and their salts may contain a centre of chirality in one or more of the side chains R, R$_1$ and Y and may therefore be obtained as a pure enantiomer, or as a mixture of enantiomers, or as a mixture containing diastereomers. Methods for asymmetric synthesis whereby the pure stereoisomers are obtained are well known in the art, e.g. synthesis with chiral induction or starting from chiral intermediates, enantioselective enzymatic conversions, separation of stereoisomers or enantiomers using chromatography on chiral media. Such methods are for example described in *Chirality in Industry* (edited by A. N. Collins, G. N. Sheldrake and J. Crosby, 1992; John Wiley).

The compounds of the invention were found to be inhibitors of human Cathepsins K and S and can therefore in a further aspect of the invention be used in therapy, and especially for the preparation of a medicament for the treatment of osteoporosis, atherosclerosis and related Cathepsin K and Cathepsin S dependent disorders, e.g. inflammation and immune disorders such as rheumatoid arthritis, chronic pain such as neuropathic pain, and further disorders related to abnormal bone resorption such as Paget's disease, osteoarthritis, osteolytic bone cancer and metastatic bone disease.

The compounds of the invention may be administered enterally or parenterally, and for humans preferably in a daily dosage of 0.001-100 mg per kg body weight, preferably 0.01-10 mg per kg body weight. Mixed with pharmaceutically suitable auxiliaries, e.g. as described in the standard reference, Gennaro et al., Remington's Pharmaceutical Sciences, (20th ed., Lippincott Williams & Wilkins, 2000, see especially Part 5: Pharmaceutical Manufacturing) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

The invention is further illustrated by the following examples.

Methods

General Chemical Procedures. All reagents were either purchased from common commercial sources or synthesised according to literature procedures using commercial sources. Proton NMR ($^1$H NMR) were obtained on a Bruker DPX 400 spectrometer and are referenced to internal tetramethylsilane (TMS). Mass spectra were recorded on a Shimadzu LC-8A (HPLC) PE Sciex API 150EX LCMS. Analytical reversed-phase LCMS analysis was carried out on LUNA C18 column (5μ; 30×4.6 mm) under gradient conditions (90% water/0.1% formic acid to 90% acetonitrile/0.1% formic acid) at a flow rate of 4 ml/min.

Abbreviations

Metachloroperoxybenzoic acid (MCPBA), dimethylformamide (DMF), N-methylpyrolidinone (NMP), dichloromethane (DCM), dimethylsulfoxide (DMSO), tetrahydrofuran (THF), 1,2-dimethoxyethane (DME), high pressure liquid chromatography (HPLC), diisopropylethylamine (DIPEA), triethylamine (TEA), broad (br), singlet (s), doublet (d), triplet (t), trifluoroacetic acid (TFA), tert-butyloxycarbonyl (Boc), 1-(3-dimethylaminopropyl)-3-ethyl carbodiimide HCl (EDCI), 1-hydroxybenzotriazole (HOBt), 2,2,6,6-tetramethyl-1-piperidinyloxy (TEMPO).

EXAMPLE 1

4-(Piperazin-1-yl)-6-(3-trifluoromethylphenyl)-pyrimidine-2-carbonitrile

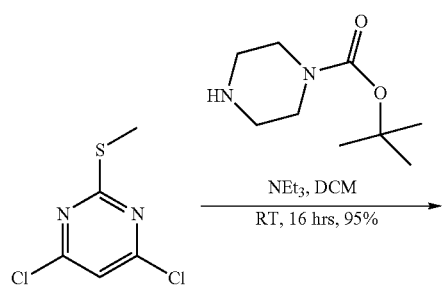

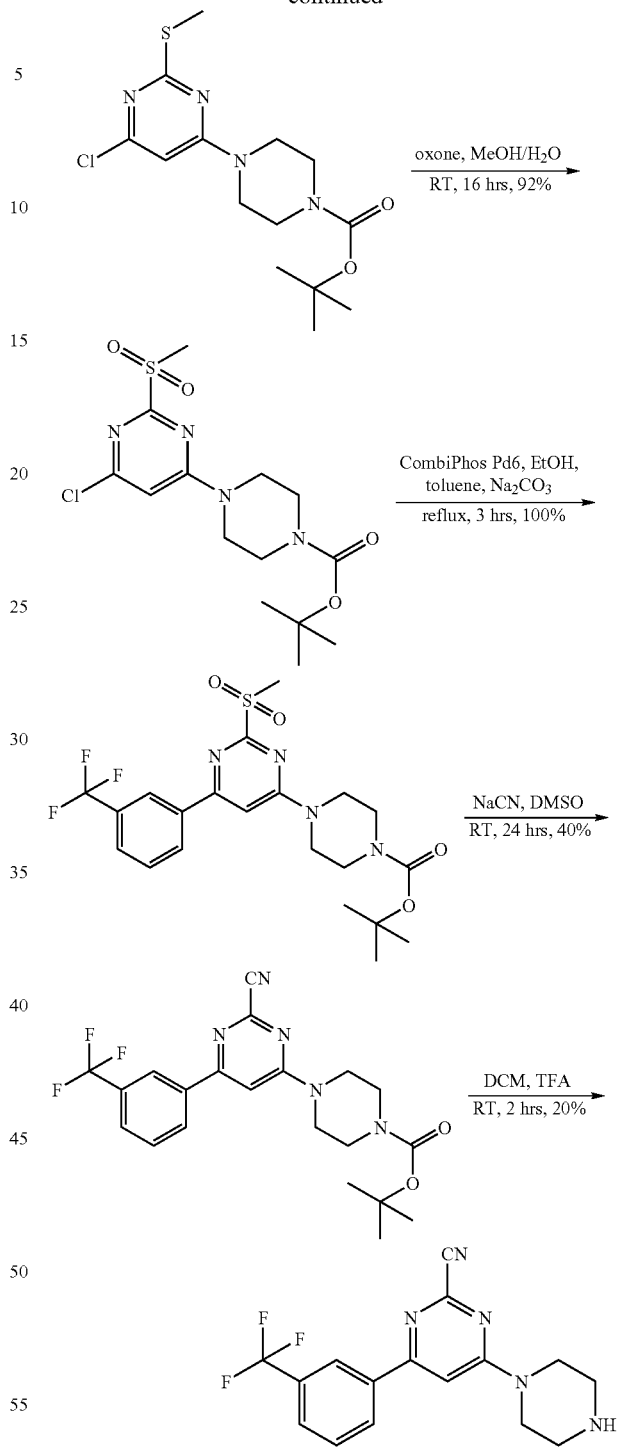

A: 4-(6-chloro-2-methylsulfanyl-pyrimidin-4-yl)-piperazine-1-carboxylic acid tert-butyl ester 4,6-Dichloro-2-methylsulfanylpyrimidine (10 g) was dissolved in dichloromethane (200 ml) and triethylamine (20.6 g) was added. The mixture was stirred at room temperature and piperazine-1-carboxylic acid tert-butyl ester (9.54 g) was added in portions. The mixture was stirred at room temperature overnight. Mixture was washed with water (200 ml) then brine (100 ml). The organic layer was dried (MgSO$_4$) then evaporated under reduced pressure to afford 4-(6-chloro-2-methylsulfanyl-pyrimidin-4-yl)-piperazine-1-carboxylic acid tert-butyl ester (17.9 g) as a white solid. $^1$H NMR (CDCl$_3$): δ 6.11 (s, 1H), 3.58 (m, 4H), 3.44 (m, 4H), 2.42 (s, 3H), 1.41 (s, 9H).

B: 4-(6-chloro-2-methanesulfonyl-pyrimidin-4-yl)-piperazine-1-carboxylic acid tert-butyl ester To a stirred solution of 4-(6-chloro-2-methylsulfanyl-pyrimidin-4-yl)-piperazine-1-carboxylic acid tert-butyl ester (1 g) in a 10:1 mixture of methanol and water (25 ml) was added oxone® (potassium peroxymonosulfate; 4.1 g). The resulting suspension was stirred at room temperature for 16 hrs. After diluting with water (100 ml), product was extracted into ethyl acetate (100 ml×3) and combined organics were washed with brine (100 ml), dried over MgSO$_4$ and concentrated in vacuo to give 4-(6-chloro-2-methanesulfonyl-pyrimidin-4-yl)-piperazine-1-carboxylic acid tert-butyl ester as a white solid (1.01 g).
$^1$H NMR (CDCl$_3$): δ 6.60 (s, 1H), 3.63-3.85 (br s, 4H), 3.54-3.59 (m, 4H), 3.28 (s, 3H), 1.49 (s, 9H); MS m/z 377.4 (M+1), 100%.

C: 4-[2-methanesulfonyl-6-(3-trifluoromethylphenyl)-pyrimidin-4-yl]-piperazine-1-carboxylic acid tert-butyl ester To a stirring solution of 4-(6-chloro-2-methanesulfonyl-pyrimidin-4-yl)-piperazine-1-carboxylic acid tert-butyl ester (500 mg) in a 1:1 mixture of ethanol and toluene (10 ml) was added 3-(trifluoromethyl)phenylboronic acid (277 mg), sodium carbonate (422 mg), water (500 μl) and CombiPhos-Pd6 (30.5 mg) catalyst mixture. The resulting suspension was heated at reflux for 3 hrs before being filtered through celite and concentrated in vacuo to give 4-[2-methanesulfonyl-6-(3-trifluoromethyl-phenyl)-pyrimidin-4-yl]-piperazine-1-carboxylic acid tert-butyl ester as a yellow oil (720 mg).
$^1$H NMR (CDCl$_3$): δ 8.24 (d, 1H), 8.21 (s, 1H), 7.77 (d, 1H), 7.63 (t, 1H), 6.97 (s, 1H), 3.83 (br s, 4H), 3.59-3.62 (m, 4H), 3.37 (s, 3H), 1.50 (s, 9H). MS m/z 487.4 (M+1), 100%.

D: 4-(4-tert-butoxycarbonyl-piperazin-1-yl)-6-(3-trifluoromethyl-phenyl)-pyrimidine-2-carbonitrile To a stirring solution of 4-[2-methanesulfonyl-6-(3-trifluoromethyl-phenyl)-pyrimidin-4-yl]-piperazine-1-carboxylic acid tert-butyl ester (720 mg) in dimethyl sulphoxide (17 ml) was added sodium cyanide (72.5 mg). The resulting solution was stirred at room temperature for 24 hrs. After diluting with ethyl acetate (100 ml), then washed with water (4×50 ml), brine (50 ml), dried over MgSO$_4$ and concentrated in vacuo. The residual solid was columned on silica gel using heptane and ethyl acetate (2:1) as eluant to give a white solid (230 mg).
$^1$H NMR (CDCl$_3$): δ 8.21 (s, 1H), 8.20 (d, 1H), 7.76 (d, 1H), 7.62 (t, 1H), 6.97 (s, 1H), 3.78 (br s, 4H), 3.59 (m, 4H), 1.50 (s, 9H). MS m/z: 434.3 (M+1), 100%.

E: 4-(piperazin-1-yl)-6-(3-trifluoromethylphenyl)-pyrimidine-2-carbonitrile trifluoroacetic acid salt To a stirring solution of 4-(4-tert-butoxycarbonyl-piperazin-1-yl)-6-(3-trifluoromethyl-phenyl)-pyrimidine-2-carbonitrile (50 mg) in dichloromethane (1 ml) was added trifluoroacetic acid (250 μl). The resulting solution was stirred at room temperature for 2 hrs. Reaction mixture was concentrated in vacuo and the residue was dissolved in acetonitrile and purified using the prep-HPLC to give the title compound trifluoroacetic acid salt as a white solid (6 mg).
$^1$H NMR (MeOD): δ 8.44 (s, 1H), 8.39 (d, 1H), 7.83 (d, 1H), 7.73 (t, 1H), 7.59 (s, 1H), 4.10-4.13 (m, 4H), 3.36-3.39 (m, 4H). MS m/z: 334.0 (M+1), 100%.

EXAMPLE 2a

4-[4-(2-Methoxy-ethyl)-piperazin-1-yl]-6-(3-trifluoromethy-phenyl)-pyrimidine-2-carbonitrile

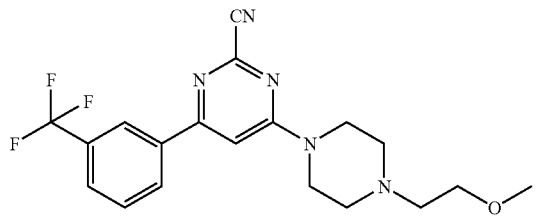

To a stirring solution of 4-(piperazin-1-yl)-6-(3-trifluoromethylphenyl)-pyrimidine-2-carbonitrile trifluoroacetic acid salt (Example 1; 100 mg) and diisopropylethylamine (78 μl) in acetonitrile (3 ml) was added 2-bromoethylmethylether (31 μl). The resulting solution was stirred at room temperature for 16 hrs, followed by heating at 45° C. for 24 hrs. Polymer bound isocyanate (1 mmol/g, 300 mg) was then added and the mixture was shaken at room temperature for 72 hrs before filtering and concentrating in vacuo. Residue was dissolved in dimethylsulphoxide and purified using the prep-HPLC to give 4-[4-(2-methoxyethyl)piperazin-1-yl]-6-(3-trifluoromethylphenyl)-pyrimidine-2-carbonitrile trifluoroacetic acid salt as a white solid (8 mg).
$^1$H NMR (MeOD): δ 8.44 (s, 1H), 8.39 (d, 1H), 7.84 (d, 1H), 7.73 (t, 1H), 7.61 (s, 1H), 3.77 (m, 2H), 3.45 (s, 3H), 3.43 (m, 2H), 3.10-3.75 (m, 8H). MS m/z: 392.3 (M+1), 100%.

The following compound was synthesised by using the same procedure.

2b: 4-(4-carbamoylmethyl-piperazin-1-yl)-6-(3-trifluoromethyl-phenyl)-pyrimidine-2-carbonitrile $^1$H NMR (MeOD): δ 8.44 (s, 1H), 8.39 (d, 1H), 7.84 (d, 1H), 7.73 (t, 1H), 7.60 (s, 1H), 3.98 (s, 2H), 3.20-3.65 (m, 8H). MS m/z 391.5 (M+1), 100%.

EXAMPLE 3

4-(4-Isopropyl-piperazin-1-yl)-6-(trifluoromethyl-phenyl)-pyrimidine-2-carbonitrile To a solution of 4-(piperazin-1-yl)-6-(3-trifluoromethylphenyl)-pyrimidine-2-carbonitrile trifluoroacetic acid salt (Example 1; 50 mg) in acetonitrile (1 ml) was added diisopropylethylamine (39 μl) and 2-bromopropane (15.5

μl). The resulting solution was subjected to microwave heating at 150° C. for 5 mins. Sodium iodide (2 mg) was added and the reaction mixture was subjected to further heating at 180° C. for 30 mins. Reaction mixture was concentrated in vacuo and the residue was dissolved in methanol and purified using the prep-HPLC to give 4-(4-isopropyl-piperazin-1-yl)-6-(trifluoromethyl-phenyl)-pyrimidine-2-carbonitrile trifluoroacetic acid salt (10 mg).

$^1$H NMR (MeOD): δ 8.44 (s, 1H), 8.39 (d, 1H), 7.84 (d, 1H), 7.72 (t, 1H), 7.61 (s, 1H), 3.62 (m, 1H), 3.18-3.60 (br s, 8H), 1.42 (d, 6H). MS m/z 376.5 (M+1), 100%.

EXAMPLE 4

4-[4-(2-tert-butyloxycarbonylethyl)-piperazin-1-yl]-6-(3-trifluoromethyl-phenyl)pyrimidine-2-carbonitrile

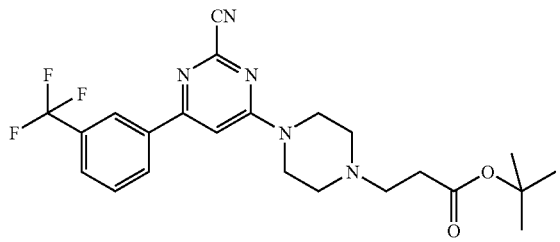

4-(Piperazin-1-yl)-6-(3-trifluoromethylphenyl)-pyrimidine-2-carbonitrile trifluoroacetic acid salt (112 mg), tert-butyl acrylate (49 μl), diisopropylethylamine (59 μl) and dimethylformamide (0.2 ml) were combined and stirred at 45° C. for 16 hrs. After adding methanol, product was purified by using the prep-HPLC to generate 4-[4-(2-tert-butoxycarbonyl-ethyl)-piperazin-1-yl]-6-(3-trifluoromethyl-phenyl)-pyrimidine-2-carbonitrile trifluoroacetic acid salt as a white solid (30 mg).

$^1$H NMR (MeOD): δ 8.44 (s, 1H), 8.39 (d, 1H), 7.84 (d, 1H), 7.72 (t, 1H), 7.61 (s, 1H), 3.8-4.3 (m, 4H), 3.41-3.58 (m, 6H), 2.85 (t, 2H), 1.50 (s, 9H). MS m/z: 462.3 (M+1), 100%.

EXAMPLE 5

4-[4-(2-carboxy-ethyl)-piperazin-1-yl]-6-(3-trifluoromethyl-phenyl)-pyrimidine-2-carbonitrile trifluoroacetic acid salt To a stirring solution of the compound of Example 4 (22 mg) in dichloromethane (2 ml) was added trifluoroacetic acid (1 ml). The resulting solution was stirred at room temperature for 1 hr before concentrating in vacuo. The residue was then purified using preparative HPLC to give 4-[4-(2-carboxy-ethyl)-piperazin-1-yl]-6-(3-trifluoromethyl-phenyl)-pyrimidine-2-carbonitrile trifluoroacetic acid salt as a white solid (8.5 mg).

$^1$H NMR (MeOD): δ 8.44 (s, 1H), 8.39 (d, 1H), 7.84 (d, 1H), 7.72 (t, 1H), 7.61 (s, 1H), 4.0-4.21 (br s, 4H), 3.42-3.55 (br m, 6H), 2.87-2.93 (t, 2H). MS m/z: 406.5 (M+1), 100%.

EXAMPLE 6

4-(4-Cyclopropylmethyl-piperazin-1-yl)-6-(trifluoromethyl-phenyl)-pyrimidine-2-carbonitrile trifluoroacetic acid salt

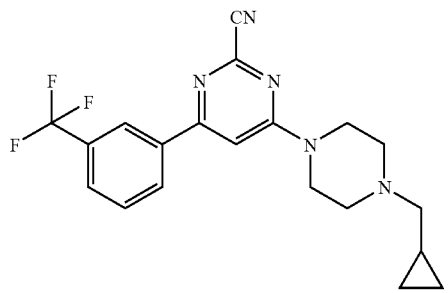

To a stirring solution of 4-(piperazin-1-yl)-6-(3-trifluoromethylphenyl)-pyrimidine-2-carbonitrile trifluoroacetic acid salt (67 mg) in methanol (2 ml) was added cyclopropane carboxaldehyde (13 μl), acetic acid (0.5 ml) and resin-bound cyanoborohydride (1 mmol/g, 89 mg). The reaction mixture was stirred at room temperature for 16 hrs. Resin was filtered off and the filtrate was concentrated in vacuo. The residue was dissolved in methanol and purified using the prep-HPLC to give 4-(4-cyclopropylmethyl-piperazin-1-yl)-6-(trifluoromethyl-phenyl)-pyrimidine-2-carbonitrile trifluoroacetic acid salt as a white solid (10 mg).

$^1$H NMR (MeOD): δ 8.44 (s, 1H), 8.40 (d, 1H), 7.84 (d, 1H), 7.73 (t, 1H), 7.62 (s, 1H), 3.1-4.0 (br s, 8H), 3.14 (t, 2H), 1.18 (m, 1H), 0.83 (m. 2H), 0.48 (m, 2H). MS m/z: 388.3 (M+1), 100%.

The following compounds were also synthesised by using the same procedure.

EXAMPLE 8

4-(4-Cyclopropyl-piperazin-1-yl)-6-(trifluoromethyl-phenyl)-pyrimidine-2-carbonitrile hydrochloric acid salt

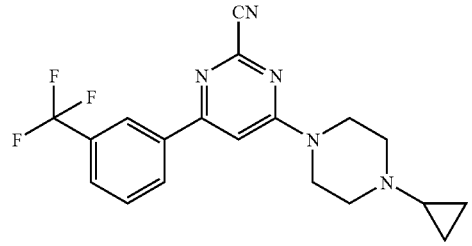

To a stirring solution of 4-(piperazin-1-yl)-6-(3-trifluoromethylphenyl)-pyrimidine-2-carbonitrile (100 mg) in methanol (2 ml) were added (1-ethoxycyclopropoxy)trimethylsilane (360 μl), acetic acid (173 μl) and sodium cyanoborohydride (85 mg). The resulting suspension was heated at reflux for 2 hrs. The mixture was diluted with dichloromethane (20 ml) and washed with water (3×20 ml) and brine (20 ml), dried over MgSO$_4$ and concentrated in vacuo to give a yellow solid which was columned on silica gel using heptane and ethyl acetate to give 85 mg of 4-(4-cyclopropyl-piperazin-1-yl)-6-(trifluoromethyl-phenyl)-pyrimidine-2-carbonitrile. Hydrochloric acid (1:1) salt was prepared by treatment with HCl in ether (1M) as a white solid.

¹H NMR (MeOD): δ 8.44 (s, 1H), 8.39 (d, 1H), 7.84 (d, 1H), 7.73 (t, 1H), 7.62 (s, 1H), 3.50-3.68 (m, 8H) 1.31 (t, 1H), 1.08-1.12 (br s, 2H), 0.98-1.03 (m, 2H). MS m/z 374.3 (M+1), 100%.

EXAMPLE 9

4-(2-Hydroxyethylamino)-6-(3-trifluoromethyl-phenyl)-pyrimidine-2-carbonitrile

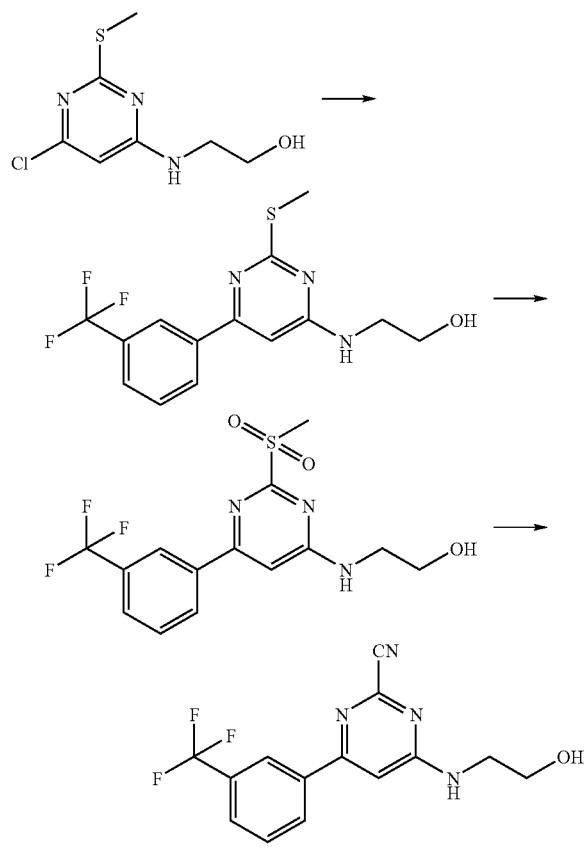

A: 2-(6-chloro-2-methylsulfanyl-pyrimidin-4-yl-amino)-ethanol

To the solution of 4,6-dichloro-2-methylsulfanylpyrimidine (9.75 g) in methanol (150 ml) was added aminoethanol (3.1 g) and triethylamine (7.5 ml). The mixture was stirred at room temperature for 20 hrs. After removal of solvent under vacuo, the residue was dissolved in isopropanol (15 ml) and ether (30 ml) was then added. The product was collected by filtration.

¹H NMR (MeOD): δ 6.15 (s, 1H), 3.69 (t, 2H), 3.50 (br, 2H).

B: 2-[2-methylsulfanyl-6-(3-trifluoromethyl-phenyl)-pyrimidin-4-yl-amino]-ethanol To a mixture of 2-(6-chloro-2-methylsulfanyl-pyrimidin-4-yl-amino)-ethanol (404 mg), 3-(trifluoromethyl)phenyl boronic acid (384 mg) and sodium carbonate (585 mg) in toluene (12 ml) with a few drops of DME and ethanol, was added Pd(PPh₃)₄ (106 mg). The resulting suspension was subjected to microwave heating at 150° C. for 20 mins. Reaction mixture was filtered through a celite pad, washed with ethyl acetate and concentrated in vacuo. The residual brown gum was columned on silica gel using heptane and ethyl acetate (1:1) as eluant. Product obtained was dissolved in tetrahydrofuran and stirred with 3-amino-1,2-propanediol at room temperature for 30 mins then diluted with ethyl acetate (40 ml) and washed with 1M hydrochloric acid (2×100 ml), brine (40 ml), dried over MgSO₄ and concentrated in vacuo to give 200 mg of 2-[2-methylsulfanyl-6-(3-trifluoromethyl-phenyl)-pyrimidin-4-yl-amino]-ethanol as a brown gum. Remaining acidic aqueous layer was slowly neutralised and the resulting white precipitate was filtered and dried. This generated 2-[2-methylsulfanyl-6-(3-trifluoromethyl-phenyl)-pyrimidin-4-yl-amino]-ethanol as a white solid (450 mg).

¹H NMR (MeOD): δ 8.28(s, 1H), 8.19(d, 1H), 7.72(d, 1H), 7.63(t, 1H), 6.69(s, 1H), 3.75(t, 2H), 3.59(t, 2H), 2.49(s, 3H).

C: 2-[2-methanesulfonyl-6-(3-trifluoromethyl-phenyl)-pyrimidin-4-yl-amino]-ethanol To a stirring suspension of 2-[2-methylsulfanyl-6-(3-trifluoromethyl-phenyl)-pyrimidin-4-yl-amino]-ethanol (450 mg) in a 10:1 acetonitrile/water mixture (11 ml) was added oxone (1.93 g). The resulting suspension was stirred at room temperature for 4.5 hrs. After diluting with ethyl acetate (100 ml), washed with water (100 ml), brine (50 ml), dried over MgSO₄ and concentrated in vacuo to give the title compound as a yellow gum (493 mg).

¹H NMR (MeOD): δ 8.31(s, 1H), 8.29(s, 1H), 7.79(d, 1H), 7.69(t, 1H), 7.14 (s, 1H), 3.76(t, 2H), 3.64(m, 2H), 3.37(s, 3H).

D: 4-(2-hydroxy-ethylamino)-6-(3-trifluoromethylphenyl)-pyrimidine-2-carbonitrile To a stirring solution of 2-[2-methanesulfonyl-6-(3-trifluoromethyl-phenyl)-pyrimidin-4-yl-amino]-ethanol (493 mg) in dimethyl sulfoxide (15 ml) was added sodium cyanide (100 mg). The resulting solution was stirred at room temperature for 72 hrs. After diluting with ethyl acetate (100 ml) and washed with water (100 ml), brine (100 ml), dried over MgSO₄ and concentrated in vacuo to give the title compound as a pale yellow solid (380 mg).

¹H NMR (MeOD): δ 8.30(s, 1H), 8.22(s, 1H), 7.80(d, 1H), 7.71(t, 1H), 7.16 (s, 1H), 3.74(t, 2H), 3.64(t, 2H), 3.37(t, 2H).

EXAMPLE 10

4-(2-morpholin-4-yl-ethylamino)-6-(3-trifluoromethyl-phenyl)-pyrimidine-2-carbonitrile A: To a stirring solution of 4-(2-hydroxy-ethylamino)-6-(3-trifluoromethyl-phenyl)-pyrimidine-2-carbonitrile (308 mg) in dichloromethane (5 ml) was added Dess-Martin periodinane (424 mg) and the resulting suspension was stirred at room temperature for 45 mins. Reaction mixture was diluted with dichloromethane (50 ml) and washed with water (3×50 ml), brine (50 ml), dried over MgSO₄ and concentrated in vacuo. The residue was filtered through silica gel pad using heptane and ethyl acetate (1:1) as eluant, solvent was removed in vacuo to give 4-(2-oxo-ethylamino)-6-(3-trifluoromethylphenyl)-pyrimidine-2-carbonitrile as a white solid (206 mg) MS m/z: 307.5 (M+1).

B: To 100 mg of above product in methanol (2 ml) was added morpholine (57 µl), acetic acid (0.5 ml) and resin-bound cyanoborohydride (190 mg). The reaction mixture was stirred at room temperature for an hour before the resin was filtered off and the product was concentrated in vacuo. The residue was dissolved in methanol and purified using the prep-HPLC to give 4-(2-morpholin-4-yl-ethylamino)-6-(3-trifluoromethyl-phenyl)-pyrimidine-2-carbonitrile trifluoroacetic acid salt as a white solid (26 mg).

$^1$H NMR (MeOD): δ 8.33 (s, 1H), 8.29 (d, 1H), 7.83 (d, 1H), 7.74 (t, 1H), 7.25 (s, 1H), 3.78-4.15 (br s, 4H), 3.91 (t, 2H), 3.25-3.72 (br s, 4H), 3.45 (t, 2H). MS m/z 378.5 (M+1), 100%.

EXAMPLE 11

4-(3,3,4-Trimethyl-4-oxy-piperazin-1-yl)-6-(3-trifluoromethyl-phenyl)-pyrimidine-2-carbonitrile

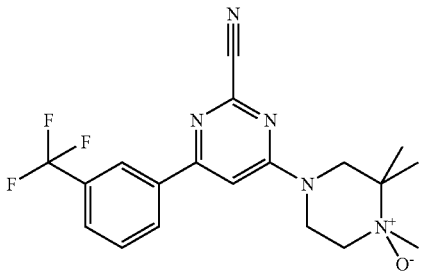

A: 2-Methylsulfanyl-6-(3-trifluoromethylphenyl)-pyrimidin-4-ylamine

To a stirred solution of 4-amino-6-chloro-2-methylthiopyrimidine (3.5 g) in toluene (45 mL) under a nitrogen atmosphere was added, sequentially, 3-(trifluoromethyl)phenylboronic acid (4.15 g), potassium carbonate (25 mL, 2M) and tetrakis(triphenylphosphine)palladium(0) (1.16 g). The mixture was heated to reflux for ten hours. Ethyl acetate (150 mL) was added and the mixture washed with water (2×100 mL). Organic layer was separated, washed with saturated sodium chloride (100 mL), dried over sodium sulphate and solvent was evaporated under reduced pressure to yield crude product. Purification by flash chromatography yielded product 2-methylsulfanyl-6-(3-trifluoromethyl-phenyl)-pyrimidin-4-ylamine (3.45 g)

$^1$H NMR (CDCl$_3$): δ 8.25 (s, 1H), 8.19 (d, 1H), 7.70 (d, 1H), 7.58 (t, 1H), 6.56 (s, 1H), 4.92 (s, 2H), 2.61 (s, 3H). MS m/z: 286.3 (M+1).

B: 2-Methylsulfanyl-6-(3-trifluoromethylphenyl)-pyrimidin-4-ol

2-Methylsulfanyl-6-(3-trifluoromethylphenyl)-pyrimidin-4-ylamine (2.42 g) was heated to 40° C. in acetic acid (6 ml) until dissolved. A solution of sodium nitrite (1.17 g in 5 ml water) was added dropwise and stirring continued for 30 minutes at 40° C. and 90 minutes at 90° C. The reaction mixture was allowed to cool to room temperature and filtered. The cake was washed with water then dissolved in ethyl acetate (200 mL) and washed with saturated sodium bicarbonate (2×300 ml). Organics were separated, dried over sodium sulphate and solvent was evaporated under reduced pressure to yield product 2-methylsulfanyl-6-(3-trifluoromethyl-phenyl)-pyrimidin-4-ol (2.11 g) as a pale yellow solid.

$^1$H NMR (CDCl$_3$): 08.30 (s, 1H), 8.18 (d, 1H), 7.71 (d, 1H), 7.61 (t, 1H), 6.70 (s, 1H), 2.72 (s, 3H).

C: 4-Chloro-2-methylsulfanyl-6-(3-trifluoromethylphenyl)-pyrimidine

2-Methylsulfanyl-6-(3-trifluoromethyl-phenyl)-pyrimidin-4-ol (500 mg) and phosphorous oxychloride (2.5 ml) were heated to reflux for four hours. The reaction mixture was concentrated under reduced pressure and the remaining residue dissolved in ethyl acetate (50 ml) and washed with water (2×30 ml). Organics were separated, dried over sodium sulphate and solvent was removed under reduced pressure to yield 4-chloro-2-methylsulfanyl-6-(3-trifluoromethyl-phenyl)-pyrimidine (478 mg) as a brown solid.

$^1$H NMR (CDCl$_3$): 08.35 (s, 1H), 8.28 (d, 1H), 7.78 (d, 1H), 7.67 (t, 1H), 7.41 (s, 1H), 2.66 (s, 3H).

D: 2-Methylsulfanyl-4-(3,3,4-trimethylpiperazin-1-yl)-6-(3-trifluoromethylphenyl)-pyrimidine 4-Chloro-2-methylsulfanyl-6-(3-trifluoromethylphenyl)-pyrimidine (200 mg), 3,3,4-trimethyl-piperazine dihydrochloride (158 mg) and triethylamine (457 µl) in dichloromethane (2 ml) were stirred at room temperature overnight. The mixture was diluted with dichloromethane (30 ml) and washed with water (2×25 ml). Organics were separated, dried over sodium sulphate and solvent was evaporated under reduced pressure to yield crude product. Flash chromatography on silica yielded product 2-methylsulfanyl-4-(3,3,4-trimethyl-piperazin-1-yl)-6-(3-trifluoromethyl-phenyl)-pyrimidine (199 mg) as a pale yellow solid.

$^1$H NMR (MeOD): 08.38 (s, 1H), 8.28 (d, 1H), 7.78 (d, 1H), 7.67 (t, 1H), 6.94 (s, 1H), 3.85 (t, 2H), 3.58 (s, 2H), 2.67 (t, 2H), 2.54 (s, 3H), 2.282 (s, 3H), 1.09 (s, 6H).

E: 2-Methanesulfonyl-4-(3,3,4-trimethyl-4-oxy-piperazin-1-yl)-6-(3-trifluoromethyl-phenyl)-pyrimidine 2-Methylsulfanyl-4-(3,3,4-trimethyl-piperazin-1-yl)-6-(3-trifluoromethyl-phenyl)-pyrimidine (188 mg) and oxone (670 mg) were stirred at room temperature in a mixture of acetonitrile (3.5 ml), methanol (1 ml) and water (0.5 ml) for two hours. Solvent was evaporated under reduced pressure and the remaining residue dissolved in ethyl acetate (40 mL) and washed with saturated sodium carbonate (40 ml). Organics were separated, dried over sodium sulphate, and solvent was evaporated under reduced pressure to yield product 2-methanesulfonyl-4-(3,3,4-trimethyl-4-oxy-piperazin-1-yl)-6-(3-trifluoromethyl-phenyl)-pyrimidine. MS m/z 445.5 (M+1).

F: 4-(3,3,4-Trimethyl-4-oxy-piperazin-1-yl)-6-(3-trifluoromethyl-phenyl)-pyrimidine-2-carbonitrile 2-Methanesulfonyl-4-(3,3,4-trimethyl-4-oxy-piperazin-1-yl)-6-(3-trifluoromethyl-phenyl)-pyrimidine (117 mg) and sodium cyanide (27 mg) were heated to 45° C. in dimethylsulphoxide (1 ml) for four hours. The reaction mixture was diluted with dichloromethane (40 ml) and washed with water (3×50 ml). Organics were separated, dried over sodium sulphate and solvent was evaporated under reduced pressure to yield crude product. Purification of 20 mg of the crude product by flash chromatography on silica followed by preparative LCMS yielded 4-(3,3,4-trimethyl-4-oxy-piperazin-1-yl)-6-(3-trifluoromethyl-phenyl)-pyrimidine-2-carbonitrile (7 mg) as a white solid.

¹H NMR (MeOD): δ 8.45 (s, 1H), 8.41 (d, 1H), 7.84 (d, 1H), 7.73 (t, 1H), 7.66 (s, 1H), 4.76 (t, 1H), 4.47 (d, 1H), 4.13 (m, 1H), 3.85 (m, 3H), 3.53 (s, 3H), 1.63 (s, 3H), 1.59 (s, 3H).

EXAMPLE 12

4-(3,3,4-Trimethyl-piperazin-1-yl)-6-(3-trifluoromethyl-phenyl)-pyrimidine-2-carbonitrile

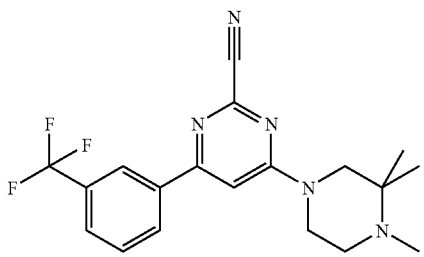

4-(3,3,4-Trimethyl-4-oxy-piperazin-1-yl)-6-(3-trifluoromethyl-phenyl)-pyrimidine-2-carbonitrile (Example 11; 16 mg) poly(methylhydrosiloxane) (8 mg) and tetrakis (triphenylphosphine)palladium(0) (5 mg) were stirred at room temperature in tetrahydrofuran (500 μl) for three hours. Tetrahydrofuran was evaporated under reduced pressure and the remaining residue dissolved in dichloromethane (5 ml) and washed with water (5 ml). Organics were separated, dried over sodium sulphate and solvent was evaporated under reduced pressure to yield crude product. Purification by preparative LCMS yielded product 4-(3,3,4-trimethyl-piperazin-1-yl)-6-(3-trifluoromethyl-phenyl)-pyrimidine-2-carbonitrile (2.5 mg) as a trifluoroacetic acid salt.

¹H NMR (MeOD): δ 8.45 (s, 1H), 8.40 (d, 1H), 7.84 (d, 1H), 7.73 (t, 1H), 7.64 (s, 1H), 3.47 (m, 3H), 3.30 (m, 3H), 2.89 (s, 3H), 1.43 (m, 6H). MS m/z 376.7 (M+1).

EXAMPLE 13

4-[1,4]Diazepan-1-yl-6-(3-trifluoromethylphenyl)-pyrimidine-2-carbonitrile

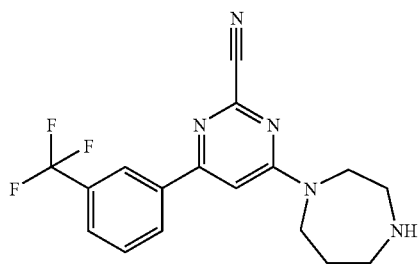

A: 4-[2-Methylsulfanyl-6-(3-trifluoromethylphenyl)-pyrimidin-4-yl]-[1,4]diazepane-1-carboxylic acid tert-butyl ester 4-Chloro-2-methylsulfanyl-6-(3-trifluoromethylphenyl)-pyrimidine (140 mg), tert-butyl 1-homopiperazinecarboxylate (181 μl) and triethylamine (320 μl) were stirred at room temperature in dichloromethane (1 ml) overnight. The reaction mixture was diluted with dichloromethane (30 ml) and washed with water (2×20 ml). Organics were separated, dried over sodium sulphate and solvent was evaporated under reduced pressure to yield crude product. Purification by flash chromatography on silica yielded product 4-[2-methylsulfanyl-6-(3-trifluoromethyl-phenyl)-pyrimidin-4-yl]-[1,4]diazepane-1-carboxylic acid tert-butyl ester (185 mg) as a yellow oil.

¹H NMR (MeOD): δ 8.19 (s, 1H), 8.12 (d, 1H), 7.68 (d, 1H), 7.57 (t, 1H), 6.50 (s, 1H), 3.80 (m, 4H), 3.59 (m, 2H), 3.38 (t, 1H), 3.27 (t, 1H), 2.57 (s, 3H), 1.99 (t, 2H), 1.42 (d, 9H).

B: 4-[2-Methanesulfonyl-6-(3-trifluoromethyl-phenyl)-pyrimidin-4-yl]-[1,4]diazepane-1-carboxylic acid tert-butyl ester 4-[2-Methylsulfanyl-6-(3-trifluoromethyl-phenyl)-pyrimidin-4-yl]-[1,4]diazepane-1-carboxylic acid tert-butyl ester (185 mg) and potassium peroxymonosulfate (558 mg) were stirred at room temperature in acetonitrile (3 ml) and water (300 μl) for eight hours. Reaction mixture was then diluted with ethyl acetate (50 ml) and washed with water (2×40 ml). Organics were separated, dried over sodium sulphate and solvent was evaporated under reduced pressure to yield product 4-[2-methanesulfonyl-6-(3-trifluoromethyl-phenyl)-pyrimidin-4-yl]-[1,4]diazepane-1-carboxylic acid tert-butyl ester (139 mg) as a yellow gum. MS m/z 501.3 (M+1).

C: 4-[1,4]Diazepan-1-yl-6-(3-trifluoromethyl-phenyl)-pyrimidine-2-carbonitrile trifluoroacetic acid salt 4-[2-Methanesulfonyl-6-(3-trifluoromethyl-phenyl)-pyrimidin-4-yl]-[1,4]diazepane-1-carboxylic acid tert-butyl ester (139 mg) and sodium cyanide (22 mg) were heated to 45° C. in dimethylsulphoxide for four hours. The reaction mixture was diluted with dichloromethane (50 ml) and washed with water (3×30 ml). Organics were separated, dried over sodium sulphate and solvent was evaporated to yield product 4-[2-cyano-6-(3-trifluoromethyl-phenyl)-pyrimidin-4-yl]-[1,4]diazepane-1-carboxylic acid tert-butyl ester (104 mg). The above product was then dissolved in dichloromethane (1 ml) and cooled to 0° C. Trifluoroacetic acid (200 μL) was added and the mixture stirred for ten minutes. Solvent was evaporated under reduced pressure to yield crude product. Purification by preparative HPLC yielded product 4-[1,4]diazepan-1-yl-6-(3-trifluoromethyl-phenyl)-pyrimidine-2-carbonitrile trifluoroacetic acid salt (52 mg) as a white solid.

¹H NMR (MeOD): δ 8.42 (s, 1H), 8.37 (d, 1H), 7.82 (d, 1H), 7.71 (t, 1H), 7.45 (s, 1H), 4.16 (m, 2H), 3.92 (m, 2H), 3.47 (t, 2H), 3.37 (t, 2H), 2.24 (m, 2H).

EXAMPLE 14

4-(4-Methyl-[1,4]diazepan-1-yl)-6-(3-trifluoromethyl-phenyl)-pyrimidine-2-carbonitrile 4-[1,4]Diazepan-1-yl-6-(3-trifluoromethyl-phenyl)-pyrimidine-2-carbonitrile trifluoroacetic acid salt (Example 13; 30 mg) and formaldehyde (6 mg, 37% wt aqueous) were stirred at room temperature in methanol (500 μl) for ten minutes. Sodium triacetoxyborohydride (17 mg) was added to the reaction and stirring continued for two hours. Solvent was evaporated under reduced pressure to yield crude product. Purification by flash chromatography on silica yielded product 4-(4-methyl-[1,4]diazepan-1-yl)-6-(3-trifluoromethyl-phenyl)-pyrimidine-2-carbonitrile (10 mg).

$^1$H NMR (MeOD): δ 8.39 (s, 1H), 8.36 (d, 1H), 7.82 (d, 1H), 7.71 (t, 1H), 7.30 (s, 1H), 4.10-3.75 (m, 4H), 2.81 (m, 2H), 2.69 (m, 2H), 2.40 (s, 3H), 2.18-1.96 (m, 2H).

MS m/z 362.5 (M+1).

EXAMPLE 15

4-Benzyloxy-6-(3-trifluoromethyl-phenyl)-pyrimidine-2-carbonitrile

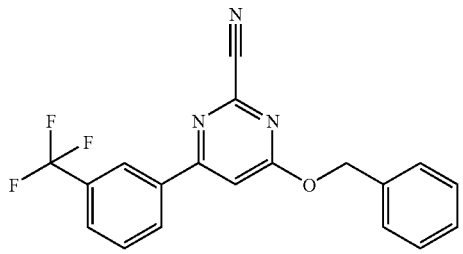

A: 2-Methylsulfanyl-6-(3-trifluoromethylphenyl)-pyrimidin-4-ylamine

To a stirred solution of 4-amino-6-chloro-2-methylthiopyrimidine (3.5 g) in toluene (45 mL) under a nitrogen atmosphere was added, sequentially, (3-trifluoromethylphenyl)boronic acid (4.15 g), potassium carbonate (25 mL, 2M) and tetrakis(triphenylphosphine)palladium(0) (1.16 g). The mixture was heated to reflux for ten hours and stirred at room temperature over the weekend. Ethyl acetate (150 mL) was added and the mixture washed with water (2×100 mL). Organics were separated, washed with saturated sodium chloride (100 mL), dried over sodium sulphate and solvent was evaporated under reduced pressure to yield crude product. Purification by flash chromatography yielded product 2-methylsulfanyl-6-(3-trifluoromethyl-phenyl)-pyrimidin-4-ylamine (3.45 g)

$^1$H NMR (CDCl$_3$): δ 8.25 (s, 1H), 8.19 (d, 1H), 7.70 (d, 1H), 7.58 (t, 1H), 6.56 (s, 1H), 4.92 (s, 2H), 2.61 (s, 3H). MS m/z 286.3 (M+1).

B: 2-Methylsulfanyl-6-(3-trifluoromethylphenyl)-pyrimidin-4-ol

2-Methylsulfanyl-6-(3-trifluoromethyl-phenyl)-pyrimidin-4-ylamine (2.42 g) was heated to 40° C. in acetic acid (6 mL) until dissolved. A solution of sodium nitrite (1.17 g in a minimum volume of water) was added dropwise and stirring continued for 30 minutes at 40° C. and 90 minutes at 90° C. The reaction mixture was allowed to cool to room temperature and filtered.

The cake was washed with water then dissolved in ethyl acetate (200 mL) and washed with saturated sodium bicarbonate (2×300 mL). Organics were separated, dried over sodium sulphate and solvent was evaporated under reduced pressure to yield product 2-methylsulfanyl-6-(3-trifluoromethylphenyl)-pyrimidin-4-ol (2.11 g) as a pale yellow solid.

$^1$H NMR (CDCl$_3$): δ 8.30 (s, 1H), 8.18 (d, 1H), 7.71 (d, 1H), 7.61 (t, 1H), 6.70 (s, 1H), 2.72 (s, 3H).

C: 4-Chloro-2-methylsulfanyl-6-(3-trifluoromethyl-phenyl)-pyrimidine

2-Methylsulfanyl-6-(3-trifluoromethyl-phenyl)-pyrimidin-4-ol (2.11 g) was heated to reflux in phosphorous oxychloride (15 mL) for four hours. Phosphorous oxychloride was evaporated under reduced pressure and the remaining residue dissolved in ethyl acetate (100 mL) and washed with saturated sodium chloride (50 mL). Organics were separated, dried over sodium sulphate and solvent was evaporated under reduced pressure to yield product 4-chloro-2-methylsulfanyl-6-(3-trifluoromethyl-phenyl)-pyrimidine (2.11 g) as a brown oil.

$^1$H NMR (CDCl$_3$): δ 8.32(s, 1H), 8.25 (d, 1H), 7.80 (d, 1H), 7.65 (t, 1H), 7.41 (s, 1H), 2.66 (s, 3H).

D: 4-Benzyloxy-2-methylsulfanyl-6-(3-trifluoromethylphenyl)-pyrimidine

To a stirred suspension of sodium hydride (630 mg, 60% dispersion in mineral oil) in tetrahydrofuran (20 ml) at 0° C. was added benzyl alcohol (1.09 ml). The mixture was stirred for 15 minutes then a solution of 4-chloro-2-methylsulfanyl-6-(3-trifluoromethyl-phenyl)-pyrimidine (1.6 g) in tetrahydrofuran (14 ml) was added dropwise. The reaction was allowed to warm to room temperature and stirred for two hours. Solvent was evaporated under reduced pressure and the remaining residue dissolved in dichloromethane (200 ml) and washed with water (2×150 ml). Organics were separated, dried over sodium sulphate and solvent was removed under reduced pressure to yield crude product (2.5 g). Flash chromatography on silica yielded product 4-benzyloxy-2-methylsulfanyl-6-(3-trifluoromethyl-phenyl)-pyrimidine (1.75 g) as a yellow solid.

$^1$H NMR (CDCl$_3$): δ 8.30 (s, 1H), 8.19 (d, 1H), 7.71 (d, 1H), 7.58 (t, 1H), 7.47 (d, 2H), 7.39 (m, 3H), 6.86 (s, 1H), 5.48 (s, 2H), 2.64 (s, 3H).

E: 4-Benzyloxy-2-methanesulfonyl-6-(3-trifluoromethylphenyl)-pyrimidine

4-Benzyloxy-2-methylsulfanyl-6-(3-trifluoromethyl-phenyl)-pyrimidine (100 mg) and potassium peroxymonosulfate (490 mg) were stirred at room temperature in acetonitrile (2 ml) and water (200 μl) for 20 hours. The reaction mixture was diluted with ethyl acetate (40 ml) and washed with water (40 ml). Organics were separated, dried over sodium sulphate, and solvent evaporated under reduced pressure to yield product 4-benzyloxy-2-methanesulfonyl-6-(3-trifluoromethyl-phenyl)-pyrimidine (93 mg). $^1$H NMR (CDCl$_3$): δ 8.28 (s, 1H), 8.25 (d, 1H), 7.80 (d, 1H), 7.68 (t, 1H), 7.48 (d, 2H), 7.41 (m, 3H), 7.32 (s, 1H), 5.59 (s, 2H), 3.40 (s, 3H).

F: 4-Benzyloxy-6-(3-trifluoromethyl-phenyl)-pyrimidine-2-carbonitrile

4-Benzyloxy-2-methanesulfonyl-6-(3-trifluoromethyl-phenyl)-pyrimidine (92 mg) and sodium cyanide (22 mg) were stirred at room temperature in dimethylsulphoxide (500 μl) for 20 minutes. The reaction mixture was diluted with dichloromethane (40 ml) and washed with water (3×50 ml). Organics were separated, dried over sodium sulphate and solvent was evaporated under reduced pressure to yield crude product (86 mg) as a yellow oil. Purification by flash chromatography on silica gave product 4-benzyloxy-6-(3-trifluoromethyl-phenyl)-pyrimidine-2-carbonitrile (54 mg).

¹H NMR (CDCl₃): δ 8.20 (s, 1H), 8.12 (d, 1H), 7.69 (d, 1H), 7.55 (t, 1H), 7.39 (d, 2H), 7.30 (m, 3H), 7.23 (s, 1H), 5.42 (s, 2H).

EXAMPLE 16a

4-Diethylamino-6-(3-trifluoromethyl-phenyl)-pyrimidine-2-carbonitrile

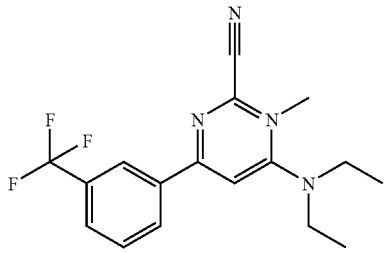

A: 4-Hydroxy-6-(3-trifluoromethylphenyl)-pyrimidine-2-carboxylic acid methyl ester To methanol (10 ml) at 0° C. was added thionyl chloride (500 ul). The mixture was stirred for 30 minutes then 4-benzyloxy-6-(3-trifluoromethyl-phenyl)-pyrimidine-2-carbonitrile (300 mg) was added and the reaction was heated to reflux for five hours. Solvent was evaporated under reduced pressure to yield crude product. Purification of the resulting residue by flash chromatography on silica afforded product 4-hydroxy-6-(3-trifluoromethylphenyl)-pyrimidine-2-carboxylic acid methyl ester (104 mg).

¹H NMR (DMSO): δ 8.41 (s, 1H), 8.40 (d, 1H), 7.89 (d, 1H), 7.78 (t, 1H), 7.36 (s, 1H), 3.93 (s, 3H).

B: 4-Hydroxy-6-(3-trifluoromethylphenyl)-pyrimidine-2-carboxylic acid amide

4-Hydroxy-6-(3-trifluoromethylphenyl)-pyrimidine-2-carboxylic acid methyl ester (17 mg) was stirred for one hour at room temperature in aqueous ammonia (500 ul). Solvent was evaporated under reduced pressure to yield product 4-hydroxy-6-(3-trifluoromethyl-phenyl)-pyrimidine-2-carboxylic acid amide (17 mg) as a white solid. ¹H NMR (DMSO): δ 8.66 (s, 1H), 8.61 (s, 1H), 8.54 (d, 1H), 8.13 (s, 1H), 7.87 (d, 1H), 7.73 (t, 1H), 7.22 (s, 1H).

C: 4-Chloro-6-(3-trifluoromethyl-phenyl)-pyrimidine-2-carbonitrile

4-Hydroxy-6-(3-trifluoromethyl-phenyl)-pyrimidine-2-carboxylic acid amide (340 mg) was heated to reflux in ethyl acetate (2 ml) and phosphorous oxychloride (8 ml) for four hours. Solvent was evaporated under reduced pressure and the remaining residue dissolved in ethyl acetate (30 ml) and washed with saturated sodium chloride (20 ml). Organics were separated, dried over sodium sulphate and solvent was removed to yield product 4-chloro-6-(3-trifluoromethylphenyl)-pyrimidine-2-carbonitrile (362 mg) as a brown solid. This product was used for next step without further purification.

D: 4-Diethylamino-6-(3-trifluoromethylphenyl)-pyrimidine-2-carbonitrile

4-Chloro-6-(3-trifluoromethylphenyl)-pyrimidine-2-carbonitrile (10 mg) dimethylamine (18 ul) and triethylamine (50 ul) were stirred at room temperature in acetonitrile (500 ul) for one hour. After removal of solvent under reduced pressure, the residue was purified by preparative LCMS to give 4-diethylamino-6-(3-trifluoromethyl-phenyl)-pyrimidine-2-carbonitrile (2.5 mg) as a white solid.

¹H NMR (MeOD): δ 8.38 (s, 1H), 8.32 (d, 1H), 7.81 (d, 1H), 7.72 (t, 1H), 7.20 (s, 1H), 3.70 (m, 4H), 1.25 (t, 6H). MS m/z 320.32 (M+1).

The procedure described above was further applied, using the appropriate amine derivatives, to prepare the following compounds:

16b: 4-(2-Pyrrolidin-1-yl-ethylamino)-6-(3-trifluoromethyl-phenyl)-pyrimidine-2-carbonitrile trifluoroacetic acid salt ¹H NMR (MeOD): δ 8.32 (s, 1H), 8.27 (d, 1H), 7.83 (d, 1H), 7.72 (t, 1H), 7.24 (s, 1H), 3.88 (t, 2H), 3.80 (m, 2H), 3.49 (t, 2H), 3.19 (m, 2H), 2.19 (m, 2H), 2.08 (m, 2H). MS m/z 362.5 (M+1).

16c: 4-(2-Dimethylamino-ethylamino)-6-(3-trifluoromethyl-phenyl)-pyrimidine-2-carbonitrile trifluoroacetic acid salt ¹H NMR (MeOD): δ 8.19 (s, 1H), 8.08 (d, 1H), 7.66 (d, 1H), 7.53 (t, 1H), 6.96 (s, 1H), 3.89 (m, 2H), 3.28 (t, 2H), 2.85 (s, 6H). MS m/z 336.3 (M+1).

16d: 4-(2-Piperidin-1-yl-ethylamino)-6-(3-trifluoromethyl-phenyl)-pyrimidine-2-carbonitrile trifluoroacetic acid salt ¹H NMR (MeOD): δ 8.32 (s, 1H), 8.27 (d, 1H), 7.82 (d, 1H), 7.71 (t, 1H), 7.23 (s, 1H), 3.88 (t, 2H), 3.70 (d, 2H), 3.37 (t, 2H), 3.02 (t, 2H), 1.97 (d, 2H), 1.83 (m, 3H), 1.54 (m, 1H). MS m/z 376.5 (M+1).

16i: 4-(3-Dimethylamino-2,2-dimethyl-propylamino)-6-(3-trifluoromethyl-phenyl)-pyrimidine-2-carbonitrile trifluoroacetic acid salt ¹H NMR (MeOD): δ 8.30 (s, 1H), 8.25 (d, 1H), 7.82 (d, 1H), 7.70 (t, 1H), 7.23 (s, 1H), 3.52 (s, 2H), 3.18 (s, 2H), 3.00 (s, 6H), 1.18 (s, 6H). MS m/z 378.7 (M+1).

16j: 4-(4-Pyrrolidin-1-yl-piperidin-1-yl)-6-(3-trifluoromethyl-phenyl)-pyrimidine-2-carbonitrile trifluoroacetic acid salt ¹H NMR (MeOD): δ 8.40 (s, 1H), 8.35 (d, 1H), 7.83 (d, 1H), 7.70 (t, 1H), 7.52 (s, 1H), 4.81 (m, 2H), 3.67 (m, 2H), 3.51 (m, 1H), 3.20 (m, 2H), 3.10 (t, 2H), 2.30 (m, 2H), 2.17 (m, 2H), 2.02 (m, 2H), 1.69 (m, 2H). MS m/z 402.5 (M+1).

16k: 4-[Methyl-(1-methyl-piperidin-4-yl)-amino]-6-(3-trifluoromethyl-phenyl)-pyrimidine-2-carbonitrile trifluoroacetic acid salt ¹H NMR (MeOD): δ 8.40 (s, 1H), 8.36 (d, 1H), 7.82 (d, 1H), 7.71 (t, 1H), 7.35 (s, 1H), 3.64 (m, 2H), 3.30 (m, 3H), 3.10 (s, 3H), 2.92 (s, 3H), 2.18 (m, 2H), 2.02 (m, 2H). MS m/z 376.7 (M+1).

16l: 4-(2-Pyridin-2-yl-ethylamino)-6-(3-trifluoromethyl-phenyl)-pyrimidine-2-carbonitrile trifluoroacetic acid salt $^1$H NMR (MeOD): δ 8.70 (d, 1H), 8.38 (t, 1H), 8.26 (s, 1H), 8.21 (d, 1H), 7.90 (d, 1H), 7.84 (m, 1H), 7.90 (d, 1H), 7.69 (t, 1H), 7.10 (s, 1H), 3.95 (t, 2H), 3.34 (t, 2H). MS m/z 370.1 (M+1).

16n: 4-[(1H-Tetrazol-5-ylmethyl)-amino]-6-(3-trifluoromethyl-phenyl)-pyrimidine-2-carbonitrile

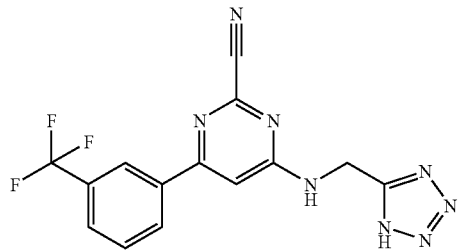

$^1$H NMR (DMSO): δ 8.57 (t, 1H), 8.28 (m, 2H), 7.89 (d, 1H), 7.79 (t, 1H), 7.43 (s, 1H), 4.94 (d, 2H). MS m/z 344.9 (M−1).

16o: 4-(Carboxymethyl-amino)-6-(3-trifluoromethyl-phenyl)-pyrimidine-2-carbonitrile $^1$H NMR (DMSO): δ 8.28 (m, 2H), 8.15 (m, 1H), 7.88 (d, 1H), 7.78 (t, 1H), 7.43 (s, 1H), 4.10 (d, 2H). MS m/z 323.5 (M+1).

16p: 4-(2-Dimethylamino-ethylsulfanyl)-6-(3-trifluoromethyl-phenyl)-pyrimidine-2-carbonitrile trifluoroacetic acid salt

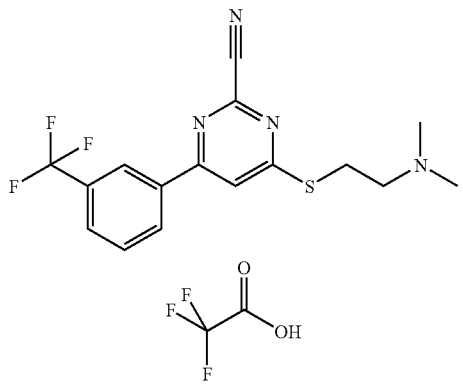

$^1$H NMR (MeOD): δ 8.63 (s, 1H), 8.58 (d, 1H), 8.28 (s, 1H), 7.89 (d, 1H), 7.78 (t, 1H), 3.61 (s, 4H), 3.03 (s, 6H). MS m/z 353.5 (M+1).

16r: 4-(Carbamoylmethyl-amino)-6-(3-trifluoromethyl-phenyl)-pyrimidine-2-carbonitrile $^1$H NMR (DMSO): δ 8.28 (m, 2H), 8.03 (t, 1H), 7.88 (d, 1H), 7.78 (t, 1H), 7.44 (s, 1H), 4.00 (d, 2H). MS m/z 322.5 (M+1).

EXAMPLE 16s 4-(2-Dimethylaminomethyl-benzylamino)-6-(3-trifluoromethyl-phenyl)-pyrimidine-2-carbonitrile trifluoroacetic acid salt $^1$H NMR (MeOD): δ 8.60 (s, 1H), 8.55 (d, 1H), 8.10 (d, 1H), 8.00 (t, 1H), 7.89-7.71 (m, 4H), 7.51 (s, 1H), 5.08 (s, 2H), 4.89 (s, 2H), 3.30 (s, 6H). MS m/z 412.5 (M+1).

EXAMPLE 17

4-(4-Methoxy-3-trifluoromethyl-phenyl)-6-piperazin-1-yl-pyrimidine-2-carbonitrile

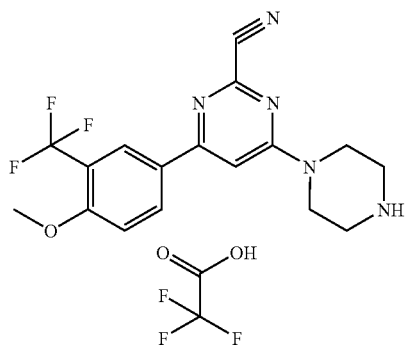

A: 3-Trifluoromethyl-4-methoxyphenyl boronic acid

3-Bromo-6-methoxy-benzotrifluoride (5 g) was dissolved in dry THF (100 ml) and the mixture was cooled to −78° C. under nitrogen. n-BuLi (12.25 ml of 1.6M solution in hexanes) was added drop wise over 10 minutes. Mixture was stirred at −78° C. for 10 minutes. Triisopropyl borate (3.87 g;) was added in one portion and the mixture was stirred at −78° C. for 30 minutes before being allowed to warm to RT. Mixture was quenched by addition of water (50 ml) and acetic acid (1 ml). Mixture was evaporated to remove THF then partitioned between DCM (100 ml) and water (50 ml). Organics were dried and evaporated under reduced pressure to afford 2.1 g of a white solid. Aqueous layer was acidified (5M HCl; 5 ml) then extracted with ethyl acetate (100 ml) to afford 1.9 g of a white solid. White solids were combined to give 4.0 g of 3-trifluoromethyl-4-methoxyphenyl boronic acid as a white solid.

$^1$H NMR (MeOH): δ 8.0-7.8 (m, 1H), 7.25-7.1 (m, 2H), 3.95 (s, 3H).

B: 4-[2-Cyano-6-(4-methoxy-3-trifluoromethyl-phenyl)-pyrimidin-4-yl]-piperazine-1-carboxylic acid tert-butyl ester 3-Trifluoromethyl-4-methoxyphenyl boronic acid (1.5 g), 4-(6-chloro-2-methylsulfanyl-pyrimidin-4-yl)-piperazine-1-carboxylic acid tert-butyl ester (2.38 g), Combiphos Pd6 (142 mg), and sodium carbonate (1.97 g) were stirred in a mixture of toluene (25 ml), ethanol (25 ml) and water (2 ml) and the mixture was heated to reflux for 1 hour. Mixture was evaporated then partitioned between ethyl acetate (200 ml) and water (200 ml) then filtered. Organics were separated then dried (MgSO$_4$) and evaporated to afford 3.4 g of a brown oil. This oil was dissolved in DMSO (50 ml), sodium cyanide was added (653 mg) and the mixture was stirred at room temperature for 72 hours. Mixture was taken up in ether (200 ml) then washed with water (2×200 ml). Organics were dried and evaporated under reduced pressure to afford 2.9 g of a brown solid. Purification by flash chromatography over silica (10% ethyl acetate/heptane to 40% ethyl acetate/heptane) gave 1.83 g of 4-[2-cyano-6-(4-methoxy-3-trifluoromethyl-phenyl)-pyrimidin-4-yl]-piperazine-1-carboxylic acid tert-butyl ester as a white solid.

$^1$H NMR (CDCl$_3$): δ 8.23 (d, 1H), 8.15 (s, 1H), 7.11 (d, 1H), 6.87 (s, 1H), 3.98 (s, 3H), 3.76 (m, 4H), 3.58 (m, 4H), 1.49 (s, 9H). MS m/z 464.3 (M+1).

C: 4-(4-Methoxy-3-trifluoromethyl-phenyl)-6-piperazin-1-yl-pyrimidine-2-carbonitrile trifluoroacetic acid salt 4-[2-Methanesulfonyl-6-(4-methoxy-3-trifluoromethyl-phenyl)-pyrimidin-4-yl]-piperazine-1-carboxylic acid tert-butyl ester (1.73 g) was dissolved in dichloromethane (50 ml) and TFA (3 ml) was added dropwise over 5 minutes. Mixture was stirred at room temperature for 30 minutes. Mixture was evaporated then coevaporated under reduced pressure with chloroform to afford 1.82 g (96%) of 4-(4-methoxy-3-trifluoromethyl-phenyl)-6-piperazin-1-yl-pyrimidine-2-carbonitrile trifluoroacetic acid salt as a white solid. $^1$H NMR (MeOH): □ 8.38 (m, 2H), 7.48 (s, 1H), 7.33 (d, 1H), 4.12 (m, 4H), 4.01 (s, 3H), 3.38 (m, 4H). MS m/z 364.3 (M+1).

EXAMPLE 18a

2-{4-[2-Cyano-6-(4-methoxy-3-trifluoromethyl-phenyl)-pyrimidin-4-yl]-piperazin-1-yl}acetamide trifluoroacetic acid salt

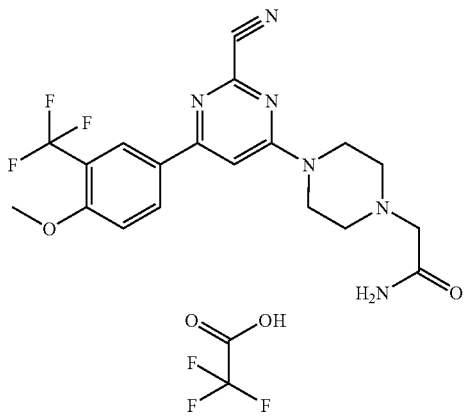

4-(4-Methoxy-3-trifluoromethyl-phenyl)-6-piperazin-1-yl-pyrimidine-2-carbonitrile trifluoroacetic acid salt (50 mg), diisopropylethylamine (40 mg) and 2-bromoacetamide (22 mg) were dissolved in acetonitrile (2 ml) and the mixture was stirred at 65° C. overnight. Mixture was partitioned between ethyl acetate (10 ml) and water (10 ml), organics were dried and evaporated under reduced pressure to afford a white solid. Purification by prep-HPLC afforded 18 mg of 2-{4-[2-Cyano-6-(4-methoxy-3-trifluoromethyl-phenyl)-pyrimidin-4-yl]-piperazin-1-yl}-acetamide trifluoroacetic acid salt as a white solid.

$^1$H NMR (MeOH): δ 8.36 (m, 2H), 7.45 (s, 1H), 7.31 (d, 1H), 4.08 (m, 4H), 3.98 (s, 3H), 3.80 (s, 2H), 3.34 (m, 4H). MS m/z 421.1 (M+1).

The following compound was also produced by using the same procedure above.

18b: 4-(4-Benzyl-piperazin-1-vi)-6-(4-methoxy-3-trifluoromethyl-phenyl)-pyrimidine-2-carbonitrile trifluoroacetic acid salt $^1$H NMR (MeOH): δ 8.35 (m, 2H), 7.53 (m, 5H), 7.48 (s, 1H), 7.33 (d, 1H), 4.5-3.6 (broad m, 4H), 4.40 (s, 2H), 3.99 (s, 3H), 3.42 (m, 4H). MS m/z 454.3 (M+1).

EXAMPLE 19

4-(2-Hydroxy-ethylamino)-6-(4-methoxy-3-trifluoromethyl-phenyl)-pyrimidine-2-carbonitrile

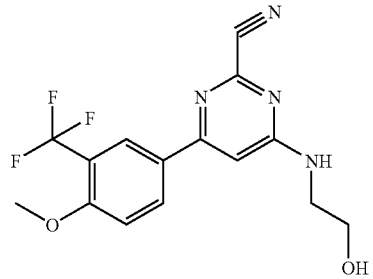

A: 2-[2-Methanesulfonyl-6-(4-methoxy-3-trifluoromethyl-phenyl)-pyrimidin-4-ylamino]-ethanol 2-(6-Chloro-2-methylsulfanyl-pyrimidin-4-ylamino)-ethanol (0.82 g), 3-trifluoromethyl-4-methoxypheyl boronic acid (1.24 g), palladium tetrakis triphenylphosphine (434 mg) and potassium carbonate (1.6 g) were dissolved in DMF (10 ml) and water (1 ml) and the mixture was heated to 150° C. for 10 minutes in a CEM Discoverer microwave. Mixture was partitioned between ethyl acetate (50 ml) and water (50 ml). Organics were dried, evaporated under reduced pressure then flash chromatographed over silica (20% ethyl acetate in heptane to 50% ethyl acetate in heptane) to afford 0.82 g of a clear oil which solidified on standing. This solid was dissolved in acetonitrile (15 ml) and water (5 ml) and stirred while Oxone was added in portions over 5 minutes. The mixture was stirred at RT for 72 hours. Mixture was evaporated under reduced pressure then partitioned between ethyl acetate (100 ml) and water (100 ml). Organics were dried (MgSO$_4$) then evaporated under reduced pressure to afford 0.68 g of 2-[2-methanesulfonyl-6-(4-methoxy-3-trifluoromethyl-phenyl)-pyrimidin-4-ylamino]-ethanol as a white solid. $^1$H NMR (CDCl$_3$): δ 8.10 (m, 2H), 7.00 (d, 1H), 6.86 (s, 1H), 6.20 (bs, 1H), 3.96 (s, 3H), 3.87 (m, 2H), 3.62 (m, 2H), 3.34 (s, 3H). MS m/z 392.5 (M+1).

B: 4-(2-Hydroxy-ethylamino)-6-(4-methoxy-3-trifluoromethyl-phenyl)-pyrimidine-2-carbonitrile 2-[2-Methanesulfonyl-6-(4-methoxy-3-trifluoromethyl-phenyl)-pyrimidin-4-ylamino]-ethanol (0.68 g) was dissolved in DMSO (10 ml) and sodium cyanide (0.17 g) was added. The mixture was stirred at RT for 48 hours. Mixture was partitioned between ethyl acetate (100 ml) and water (100 ml). Organics were dried and evaporated then flash chromatographed over silica (DCM-2% methanol in DCM) to afford 420 mg of 4-(2-Hydroxy-ethylamino)-6-(4-methoxy-3-trifluoromethyl-phenyl)-pyrimidine-2-carbonitrile as a white solid.

$^1$H NMR (MeOH): δ 8.23 (m, 2H), 7.30 (d, 1H), 7.07 (s, 1H), 3.98 (s, 3H), 3.73 (m, 2H), 3.56 (m, 2H). MS m/z 339.1 (M+1).

EXAMPLE 20

4-(4-Methoxy-3-trifluoromethylphenyl)-6-(2-morpholin-4-yl-ethylamino)-pyrimidine-2-carbonitrile

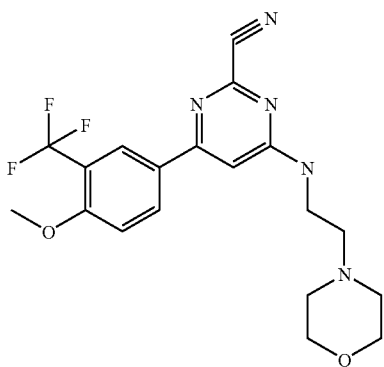

4-(2-Hydroxy-ethylamino)-6-(4-methoxy-3-trifluoromethyl-phenyl)-pyrimidine-2-carbonitrile (150 mg) was dissolved in THF (10 ml) and Dess-Martin periodinane was added in one portion. The mixture was stirred at room temperature for 1.5 hours. Mixture was evaporated under reduced pressure then flash chromatographed over silica (50% ethyl acetate in heptane) to afford 84 mg of an oily solid. 20 mg of this solid was dissolved in methanol (1 ml) and acetic acid (0.1 ml). Morpholine (13 mg) was added and the mixture was stirred at room temperature for 30 minutes. Sodium triacetoxyborohydride (24 mg) was added and the mixture was stirred at room temperature overnight. Mixture was evaporated, dissolved in acetonitrile then prep-LCMS purified to afford 4-(4-methoxy-3-trifluoromethyl-phenyl)-6-(2-morpholin-4-yl-ethylamino)-pyrimidine-2-carbonitrile as a clear oil. $^1$H NMR (CDCl$_3$): δ 8.34 (s, 1H), 8.14 (d, 1H), 7.91 (bs, 1H), 7.09 (d, 1H), 6.92 (s, 1H), 4.04 (m, 4H), 3.96 (m, 5H), 3.53 (bs, 2H), 3.32 (m, 2H), 2.96 (m, 2H). MS m/z 408.5 (M+1).

EXAMPLE 21

4-Hydroxy-6-(3-trifluoromethyl-phenyl)-pyrimidine-2-carbonitrile mCPBA (550 mg, 70% w/w) was added to a solution of 2-methylthio-6-(3-trifluoromethyl-phenyl)-pyrimidin-4-ol (200 mg, 0.75 mmol) in acetonitrile (7 ml). After 48 h, a solution of Na$_2$SO$_3$ (5 ml, 1N) was added and the reaction mixture was concentrated under reduced pressure to give 1 g of intermediate. A mixture of 238 mg of this intermediate and sodium cyanide (73 mg, 1.49 mmol) in dry DMSO (7.5 ml) was heated at 80° C. for 32 h. The solvent was removed under reduced pressure. Water (2 ml) was added to dissolve the remaining NaCN. The solid was purified by preparative HPLC to give the above titled compound (20 mg, yield 10%). HPLC: 100%. $^1$H NMR (DMSO-d$_6$) δ: 8.44 (2H, s), 7.94 (1H, d), 7.80 (1H, t), 7.71 (1H, m). MS m/z: 266 (M+1).

EXAMPLE 22a 4-(2-Piperidin-1-yl-ethoxy)-6-(3-trifluoromethyl-phenyl)-pyrimidine-2-carbonitrile

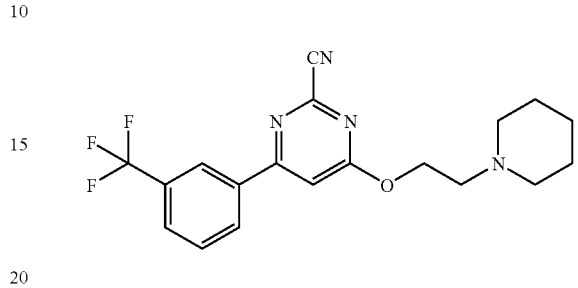

A: 2-Methylthio-4-(2-piperidin-1-yl-ethoxy)-6-(3-trifluoromethyl-phenyl)-pyrimidine Sodium hydride (30 mg, 1.23 mmol) was added to a mixture of 4-chloro-2-methylthio-6-(3-trifluoromethyl-phenyl)-pyrimidine (187 mg, 0.62 mmol) and 1-(2-hydroxyethyl)piperidine (120 μl, 0.92 mmol) in dry THF (6 ml). The mixture was heated at 40° C. for 2 h. After cooling, water and tert-butyl-methyl ether were added. The aqueous layer was extracted twice with tBuOMe. The combined organic layers were dried over MgSO$_4$ and concentrated under reduced pressure. The residue was chromatographed over silica gel (eluent: CH$_2$Cl$_2$ to CH$_2$Cl$_2$/MeOH 95/5) to yield the above titled compound: 190 mg (yield: 78%).

$^1$H NMR (CDCl$_3$) δ: 8.29 (1H, s), 8.20 (1H, d), 7.71 (1H, d), 7.59 (1H, m), 6.83 (1H, s), 4.55 (2H, m), 2.78 (2H, m), 2.62 (3H, s), 2.51 (4H, m), 1.61 (4H, m), 1.45 (2H, m).

B: 2-Methanesulfonyl-4-(2-piperidin-1-yl-ethoxy)-6-(3-trifluoromethyl-phenyl)-pyrimidine A solution of HCl (720 μl, 2N in Et$_2$O, 1.43 mmol) was added to a solution of 2-methylthio-4-(2-piperidin-1-yl-ethoxy)-6-(3-trifluoromethyl-phenyl)-pyrimidine (190 mg, 0.48 mmol) in Et$_2$O (1 ml). The solvent was evaporated and the precipitate was dissolved in a mixture of water (1 ml) and acetonitrile (6 ml). Oxone (586 mg, 0.96 mmol) was added and the reaction mixture was stirred at room temperature for 60 h. An aqueous Na$_2$CO$_3$ saturated solution (6 ml) was added (pH=9) followed by AcOEt. The organic layer was washed with Na$_2$SO$_3$, with brine, dried over MgSO4 and concentrated under reduced pressure to give the above titled compound: 184 mg (yield: 90%) which was used in the next step without any further purification.

$^1$H NMR (CDCl$_3$) δ: 8.27 (2H, m), 7.80 (1H, d, J=7.6 Hz), 7.69 (1H, d, J=8 Hz), 7.26 (1H, s), 4.67 (2H, t, J=5.6 Hz), 3.42 (3H, s), 2.79 (2H, t, J=5.6 Hz), 2.50 (4H, m), 1.59 (4H, m), 1.45 (2H, m). MS m/z: 430 (M+1).

C: 4-(2-Piperidin-1-yl-ethoxy)-6-(3-trifluoromethyl-phenyl)-pyrimidine-2-carbonitrile A mixture of 2-methanesulfonyl-4-(2-piperidin-1-yl-ethoxy)-6-(3-trifluoromethyl phenyl)-pyrimidine (50 mg, 0.12 mmol) and sodium cyanide (12 mg, 0.23 mmol) in acetonitrile (1.5 ml) with a few drops of DMSO was stirred at room temperature for 18 h. The solvent was removed under reduced pressure. The residue was chromatographed over silica gel (eluent: $CH_2Cl_2$ to $CH_2Cl_2$/MeOH 95/5) to yield 31 mg of the above titled compound, yield: 70%. HPLC: 99.5%.

$^1$H NMR (CDCl$_3$) δ: 8.31 (1H, br s), 8.24 (1H, d, J=7.6 Hz), 7.79 (1H, d, J=7.6 Hz), 7.66 (1H, t, J=7.6 Hz), 7.34 (1H, br s), 4.61 (2H, m), 2.81 (2H, m), 2.54 (4H, m), 1.63 (4H, m), 1.46 (2H, m). MS m/z: 377 (M+1).

The procedure described above was further applied, using the appropriate amine derivatives, to prepare the following compounds:

22b: 4-(2-Morpholin-4-yl-ethoxy)-6-(3-trifluoromethyl-phenyl)-pyrimidine-2-carbonitrile $^1$H NMR (CDCl$_3$) δ: 8.31 (1H, s), 8.25 (1H, d, J=8 Hz), 7.80 (1H, d, J=8 Hz), 7.66 (1H, t, J=8 Hz), 7.34 (1H, s), 4.62 (2H, t, J=5.6 Hz), 3.73 (4H, m), 2.82 (2H, t, J=5.6 Hz), 2.59 (4H, m). MS m/z: 379 (M+1).

22c: 4-(2-Diethylamino-ethoxy)-6-(3-trifluoromethyl-phenyl)-pyrimidine-2-carbonitrile $^1$H NMR (CDCl$_3$) δ: 8.31 (1H, s), 8.23 (1H, d, J=7.6 Hz), 7.79 (1H, d, J=8 Hz), 7.66 (1H, t, J=7.8 Hz), 7.32 (1H, s), 4.55 (2H, t, J=6 Hz), 2.89 (2H, t, J=6 Hz), 2.65 (4H, q, J=7.2 Hz), 1.08 (6H, t, J=7.2 Hz). MS m/z: 365 (M+1).

22d: 4-((2S)-1-Methyl-pyrrolidin-2-ylmethoxy)-6-(3-trifluoromethyl-phenyl)-pyrimidine-2-carbonitrile $^1$H NMR (CDCl$_3$) δ: 8.31 (1H, s), 8.24 (1H, d, J=8 Hz), 7.79 (1H, d, J=7.6 Hz), 7.66 (1H, t, J=7.8 Hz), 7.34 (1H, s), 4.47 (2H, m), 3.14 (1H, t, J=9 Hz), 2.66 (1H, m), 2.48 (3H, s), 2.31 (1H, m), 2.02 (1H, m), 1.70-1.90 (3H, m). MS m/z: 363 (M+1).

22e: 4-(2-tert-Butylamino-ethoxy)-6-(3-trifluoromethyl-phenyl)-pyrimidine-2-carbonitrile $^1$H NMR (CDCl$_3$) δ: 8.30 (1H, s), 8.24 (1H, d, J=8 Hz), 7.79 (1H, d, J=7.6 Hz), 7.65 (1H, t, J=7.8 Hz), 7.33 (1H, s), 4.60 (2H, t, J=5.2 Hz), 3.08 (2H, t, J=5.4 Hz), 1.20 (9H, s). MS m/z: 365 (M+1).

EXAMPLE 23

Assay Procedures

Cathepsin K Activity:

The inhibitory activity of the compounds of the invention was demonstrated in vitro by measuring the inhibition of recombinant human Cathepsin K as follows:

To a 384 well microtitre plate is added 5 μl of a 100 μM solution of test compound in assay buffer (100 mM sodium acetate pH 5.5, 5 mM EDTA, 5 mM dithiothreitol) with 10% dimethylsulfoxide (DMSO), plus 10 μl of 100 μM solution of the substratre Z-Phe-Arg-AMC (Bachem; 7-amido-coumarine derivative of the dipeptide N-benzyloxycarbonyl-Phe-Arg-OH) in assay buffer and 25 μl of assay buffer. 10 μl of a 1 mg/l solution of activated recombinant human cathepsin K, in assay buffer, is then added to the well, yielding a final inhibitor concentration of 10 μM. Enzyme activity is determined by measuring the fluorescence of the liberated aminomethylcoumarin at 440 nM using 390 nM excitation, at 10 minutes. Percentage enzyme activity is calculated by comparison of this activity to that of a solution containing no inhibitor. Compounds are subsequently subjected to a dose response curve analysis in order to determine IC$_{50}$ values for active compounds (where IC$_{50}$ is the concentration of test compound causing 50% inhibition of the enzymatic activity).

Compounds of the invention typically have a pIC$_{50}$ (negative logarithm of the IC$_{50}$ concentration) for inhibition of human cathepsin K of more than 6, preferably more than 7 and most preferably a pIC$_{50}$ of more than 8, such as for the compounds of Examples 1, 2a, 2b, 3, 5, 6, 8, 12, 14, 13, 16k, 16n, 16o, 17, 22a, 22b, 22c Cathepsin S Activity.

The inhibitory activity of the compounds of the invention was demonstrated in vitro by measuring the inhibition of recombinant human Cathepsin S as follows:

To a 384 well microtitre plate is added 10 μl of a 100 μM solution of test compound in assay buffer (100 mM sodium acetate pH 5.5, 5 mM EDTA, 5 mM dithiothreitol) with 10% dimethylsulfoxide (DMSO), plus 20 μl of 250 μM solution of the substratre Z-Val-Val-Arg-AMC (Bachem; 7-amido-coumarine derivative of the tripeptide N-benzyloxycarbonyl-Val-Val-Arg-OH) in assay buffer and 45 μl of assay buffer. 25 μl of a 2 mg/l solution of activated recombinant human cathepsin S, in assay buffer, is then added to the well, yielding a final inhibitor concentration of 10 μM.

Enzyme activity is determined by measuring the fluorescence of the liberated aminomethylcoumarin at 440 nM using 390 nM excitation, at 20 minutes. Percentage enzyme activity is calculated by comparison of this activity to that of a solution containing no inhibitor. Compounds are subsequently subjected to a dose response curve analysis in order to determine IC$_{50}$ values for active compounds (where IC$_{50}$ is the concentration of test compound causing 50% inhibition of the enzymatic activity).

Compounds of the invention typically have a pIC$_{50}$ (negative logarithm of the IC$_{50}$ concentration) for inhibition of human cathepsin S of more than 6. Most compounds of the invention have a pIC$_{50}$ of more than 7.

The invention claimed is:

1. A 4-phenyl-6-substituted-pyrimidine-2-carbonitrile compound having the general formula I

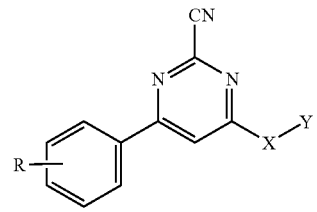

Formula I wherein

R represents 1-3 optional substituents independently selected from (C$_{1-4}$)alkyl optionally substituted with one or more halogens, (C$_{1-4}$)alkyloxy optionally substituted with one or more halogens and halogen;

X is NR$_1$, O or S;

R$_1$ is H or (C$_{1-4}$)alkyl;

Y is (C$_{1-4}$)alkyl, benzyl or (C$_{2-6}$)alkyl, substituted with a group selected from OH, (C$_{1-4}$)alkyloxy, NR$_2$R$_3$, a 4-8 membered saturated heterocyclic ring comprising 1 or 2 heteroatoms selected from O, S and $NR_4$, and a 5 or 6-membered aromatic heterocyclic group comprising 1-4 N atoms; or $R_1$ and Y form together with the nitrogen to which they are bonded a 5-8 membered saturated heterocyclic ring, optionally comprising a further heteroatom selected from O, S, $NR_4$ and NO; the ring being optionally substituted with $NR_2R_3$ or with 1 to 4 $(C_{1-3})$alkyl groups;

$R_2$ and $R_3$ are independently H or $(C_{1-4})$alkyl; or $R_2$ and $R_3$ form together with the nitrogen to which they are bonded a 4-8 membered saturated heterocyclic ring, optionally comprising a further heteroatom selected from O, S and $NR_4$;

$R_4$ is H, $(C_{1-6})$alkyl, $(C_{3-6})$cycloalkyl, $(C_{3-6})$cycloalkyl$(C_{1-4})$alkyl, $(C_{1-4})$alkyloxy$(C_{1-4})$alkyl, benzyl, amido$(C_{1-4})$alkyl, $(C_{1-6})$alkyloxycarbonyl$(C_{1-4})$alkyl or carboxy$(C_{1-4})$alkyl; or a pharmaceutically acceptable salt thereof.

2. The 4-phenyl-6-substituted-pyrimidine-2-carbonitrile compound according to claim 1, wherein R represents a trifluoromethyl substituent at the meta position of the 4-phenyl group.

3. The 4-phenyl-6-substituted-pyrimidine-2-carbonitrile compound according to claim 1, wherein X is $NR_1$.

4. The 4-phenyl-6-substituted-pyrimidine-2-carbonitrile compound according to claim 2, wherein X is $NR_1$.

5. The 4-phenyl-6-substituted-pyrimidine-2-carbonitrile compound of formula I which is selected from:

4-(piperazin-1-yl)-6-(3-trifluoromethylphenyl)-pyrimidine-2-carbonitrile;

4-(4-cyclopropyl-piperazin-1-yl)-6-(trifluoromethylphenyl)-pyrimidine-2-carbonitrile;

4-[1,4]diazepan-1-yl-6-(3-trifluoromethylphenyl)-pyrimidine-2-carbonitrile;

4-[methyl-(1-methyl-piperidin-4-yl)-amino]-6-(3-trifluoromethylphenyl)-pyrimidine-2-carbonitrile;

4-[(1H-tetrazol-5-ylmethyl)-amino]-6-(3-trifluoromethylphenyl)-pyrimidine-2-carbonitrile;

4-(4-methoxy-3-trifluoromethylphenyl)-6-piperazin-1-yl-pyrimidine-2-carbonitrile;

4-(2-piperidin-1-yl-ethoxy)-6-(3-trifluoromethylphenyl)-pyrimidine-2-carbonitrile;

4-[4-(2-methoxy-ethyl)-piperazin-1-yl]-6-(3-trifluoromethylphenyl)-pyrimidine-2-carbonitrile;

4-(4-carbamoylmethyl-piperazin-1-yl)-6-(3-trifluoromethylphenyl)-pyrimidine-2-carbonitrile;

4-(4-isopropyl-piperazin-1-yl)-6-(trifluoromethylphenyl)-pyrimidine-2-carbonitrile;

4-[4-(2-carboxy-ethyl)-piperazin-1-yl]-6-(3-trifluoromethylphenyl)-pyrimidine-2-carbonitrile;

4-(4-cyclopropylmethyl-piperazin-1-yl)-6-(trifluoromethylphenyl)-pyrimidine-2-carbonitrile;

4-(3,3,4-trimethyl-piperazin-1-yl)-6-(3-trifluoromethylphenyl)-pyrimidine-2-carbonitrile;

4-(4-methyl-[1,4]diazepan-1-yl)-6-(3-trifluoromethylphenyl)-pyrimidine-2-carbonitrile;

4-(carboxymethyl-amino)-6-(3-trifluoromethylphenyl)-pyrimidine-2-carbonitrile;

4-(2-morpholin-4-yl-ethoxy)-6-(3-trifluoromethylphenyl)-pyrimidine-2-carbonitrile;

4-(2-diethylamino-ethoxy)-6-(3-trifluoromethylphenyl)-pyrimidine-2-carbonitrile.

6. A pharmaceutical composition comprising a 4-phenyl-6-substituted-pyrimidine-2-carbonitrile compound according to claim 1, or a pharmaceutically acceptable salt thereof, in admixture with pharmaceutically acceptable auxilliaries.

7. A method of treating a cathepsin K and cathepsin S dependent disorder selected from the group consisting of osteoporosis, atherosclerosis, rheumatoid arthritis, osteoarthritis and chronic pain in a subject, the method comprising administering to the subject an effective amount of a 4-phenyl-6-substituted-pyrimidine-2-carbonitrile compound according to claim 1, or a pharmaceutically acceptable salt thereof.

8. The method of claim 7, wherein the disorder is osteoporosis.

9. The method of claim 7, wherein the disorder is atherosclerosis.

10. The method of claim 7, wherein the disorder is rheumatoid arthritis.

11. The method of claim 7, wherein the disorder is osteoarthritis.

12. The method of claim 7, wherein the disorder is chronic pain.

* * * * *